(12) United States Patent
Asch et al.

(10) Patent No.: US 9,877,700 B1
(45) Date of Patent: Jan. 30, 2018

(54) ULTRASOUND IMAGING OF ANATOMY

(71) Applicant: Asch-Klaassen Sonics, LLC, Westchester, OH (US)

(72) Inventors: Herbert A. Asch, Symmes Township, OH (US); Dan Castner, Carlsbad, CA (US); Bruce W. Hultgren, Victoria, MN (US); Richard E. Klaassen, West Chester, OH (US)

(73) Assignee: ASCH-KLAASSEN SONICS, LLC, Westchester, OH (US)

( * ) Notice: Subject to any disclaimer, the term of this patent is extended or adjusted under 35 U.S.C. 154(b) by 0 days.

(21) Appl. No.: 15/052,576

(22) Filed: Feb. 24, 2016

Related U.S. Application Data

(60) Provisional application No. 62/120,227, filed on Feb. 24, 2015.

(51) Int. Cl.
  *A61B 8/00*   (2006.01)
  *A61B 8/14*   (2006.01)
  *A61B 8/08*   (2006.01)

(52) U.S. Cl.
  CPC .......... *A61B 8/4455* (2013.01); *A61B 8/0875* (2013.01); *A61B 8/145* (2013.01); *A61B 8/4245* (2013.01); *A61B 8/4281* (2013.01); *A61B 8/4494* (2013.01); *A61B 8/461* (2013.01); *A61B 8/5207* (2013.01); *A61B 8/5246* (2013.01)

(58) Field of Classification Search
  None
  See application file for complete search history.

(56) References Cited

U.S. PATENT DOCUMENTS

| | | | | |
|---|---|---|---|---|
| 6,500,118 B1 * | 12/2002 | Hashimoto | .............. | A61B 8/00 128/916 |
| 6,638,219 B1 * | 10/2003 | Asch | ........................ | A61B 8/00 433/214 |
| 7,386,333 B1 * | 6/2008 | Birecki | ................ | A61B 5/0088 600/310 |

\* cited by examiner

*Primary Examiner* — Jonathan Cwern
(74) *Attorney, Agent, or Firm* — Brake Hughes Bellermann LLP

(57) ABSTRACT

Apparatuses, components, methods, and techniques for ultrasound imaging of patient anatomy are provided. An example system for ultrasound imaging of patient anatomy includes an ultrasound probe and a probe interface device. An example ultrasound probe includes a handle, an elongate member coupled to the handle and a two-dimensional array of ultrasound transducers coupled to the elongate member. The ultrasound transducers emit ultrasound when activated. An example probe interface device is communicatively coupled to the ultrasound probe. The example probe interface device is configured to activate at least one of the ultrasound transducers and to receive data corresponding to ultrasonic waves captured by a plurality of the ultrasound transducers.

14 Claims, 19 Drawing Sheets

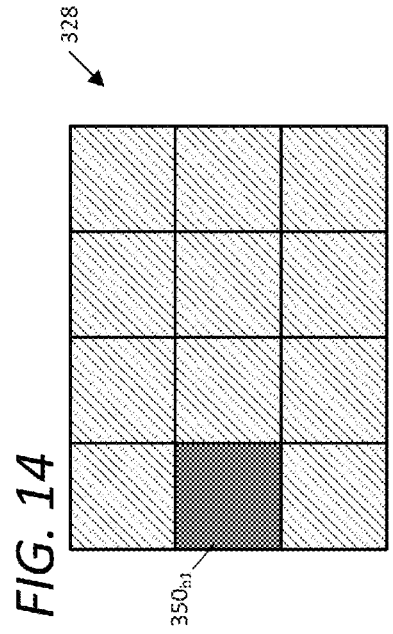
FIG. 14
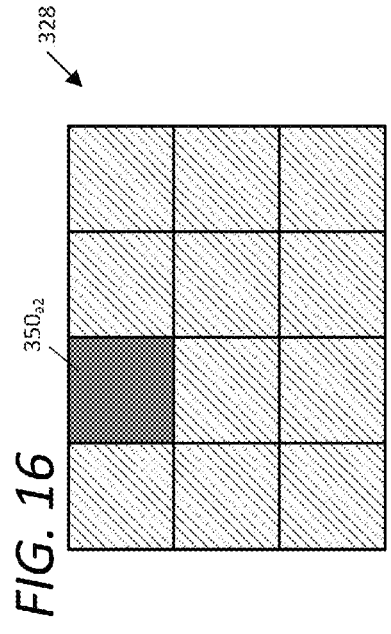
FIG. 16
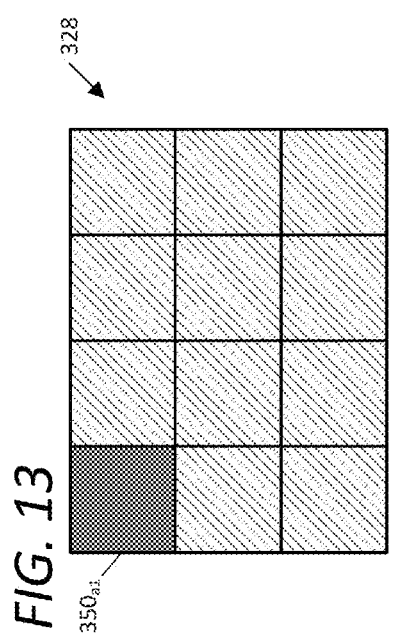
FIG. 13
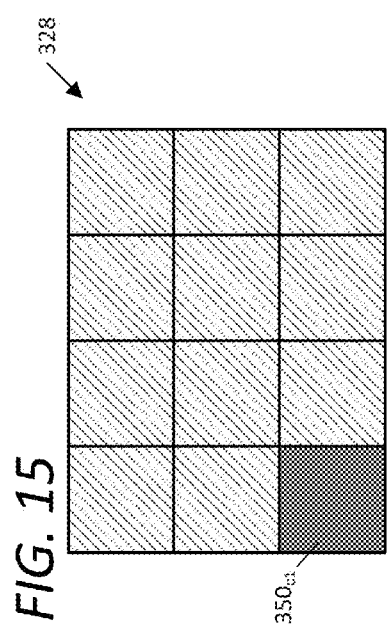
FIG. 15
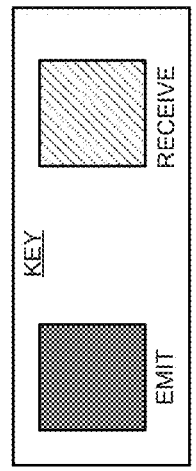

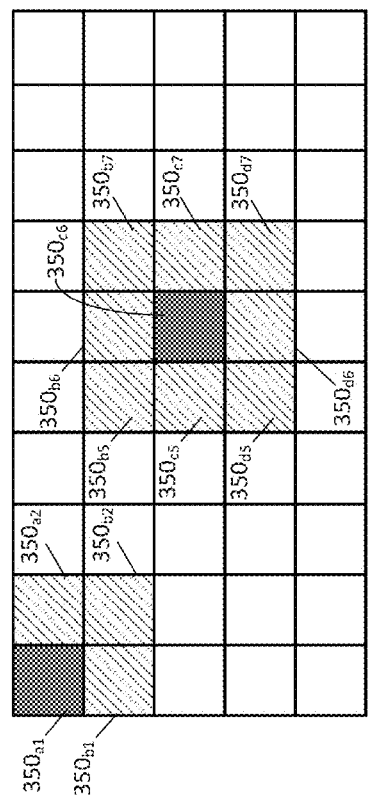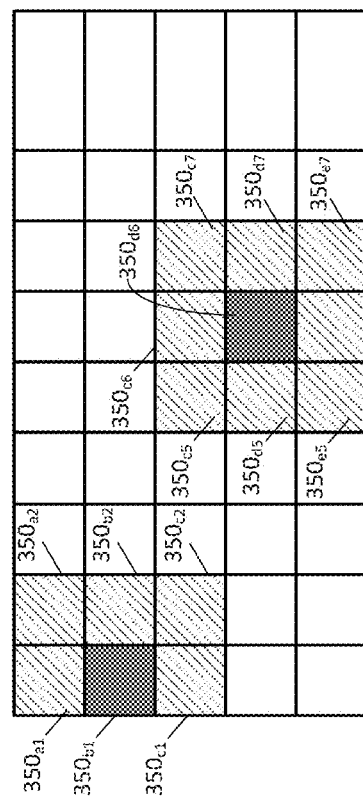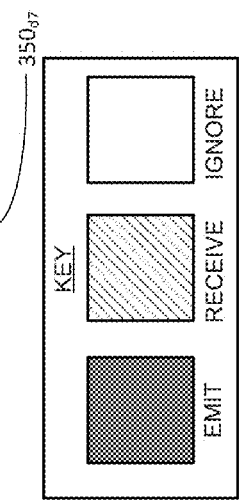
FIG. 17
FIG. 18

ULTRASOUND IMAGING OF ANATOMY

CROSS-REFERENCE TO RELATED APPLICATIONS

This application claims priority to U.S. Provisional Application Ser. No. 62/120,227, entitled "ULTRASOUND IMAGING OF ANATOMY," filed on Feb. 24, 2015, the entire disclosure of which is hereby incorporated herein by reference.

BACKGROUND

Anatomy refers to parts of the human body. For example, craniofacial anatomy includes the anatomy of a patient's skull and face, including the dental anatomy of the patient. Dental anatomy includes the anatomy of a patient's mouth, including teeth and soft tissues (e.g., gums). Other examples of anatomy include the bones and other tissues of the thorax, extremities, neck, and other parts of the human body.

Imaging of the anatomy of a patient can be useful to medical professionals, such as physicians and dentists. For example, images of the anatomy may be used to diagnose or treat certain conditions. For some conditions, it is helpful to have three-dimensional images of the anatomy.

For example, dentists often require three-dimensional dental images of the dental anatomy of a patient. One example of a three-dimensional image of dental anatomy is a dental impression. A dental impression captures the shape of at least a portion of a patient's dental anatomy. Typically, a dental impression can also be used to generate a mold of the imaged dental anatomy. This mold can then be used, for example, to fabricate a dental restoration (e.g., a crown, bridge, etc.) for the patient. The mold can also be used for many other purposes, such as planning orthodontic treatment, implant surgery, etc.

Dental impressions are often captured using a physical impressioning material, such as polyvinyl siloxane or alginate materials. These physical impressioning materials are pressed against the dental anatomy, allowed to set, and then removed. Dental images created from physical impressions can suffer from various problems. For example, bubbles can interfere with capturing the dental anatomy. Additionally, the physical impression can distort during removal or over time as the impressioning material dries out or encounters changing environmental conditions. It can also be difficult to duplicate dental images created from physical impressions as the impression is typically distorted or destroyed in the process of making a mold. In addition to capturing dental images, similar techniques can also be used to capture images of other portions of the patient's anatomy, such as an ear canal.

Ultrasound is a sound wave with a frequency greater than the upper limits of human hearing. Ultrasound can be used in medical imaging (e.g., fetal imaging). Typically, in medical imaging applications, sound waves having a frequency in the range of 1 megahertz to 18 megahertz are used.

SUMMARY

In general terms, this disclosure is directed to ultrasound imaging of anatomy, including surface and subsurface anatomy. In one possible configuration and by non-limiting example, a system for ultrasound imaging of anatomy includes a two-dimensional array ultrasound probe. Various aspects are described in this disclosure, which include, but are not limited to, the following aspects.

In an aspect, a system for ultrasound imaging of patient anatomy comprising: an ultrasound probe, comprising: a handle; an elongate member coupled to the handle; and a two-dimensional array of ultrasound transducers coupled to the elongate member, wherein the ultrasound transducers emit ultrasound when activated; and a full-matrix capture probe interface device communicatively coupled to the ultrasound probe, wherein the probe interface device is configured to activate at least one of the ultrasound transducers and to receive data corresponding to ultrasonic waves captured by a plurality of the ultrasound transducers.

In another aspect, a method of imaging anatomy using an ultrasound probe that includes a plurality of ultrasound transducers arranged in a two-dimensional array, the method comprising: receiving an input signal indicating the probe is adjacent to the target anatomy; iterating through the plurality of transducers to capture ultrasound reflection data individually, wherein capturing ultrasound reflection data comprises emitting an ultrasound pulse with a single transducer of the plurality of transducers and capturing ultrasound reflection data using multiple transducers of the plurality of transducers; generating image segments from the captured ultrasound reflection data; and merging multiple image segments to form an image.

In yet another aspect, a system for ultrasound imaging of patient dentition comprising: an ultrasound probe, comprising: a handle; an elongate member coupled to the handle; a two-dimensional array of ultrasound transducers coupled to the elongate member, wherein the ultrasound transducers emit ultrasound when activated; and a sheath coupled to the elongate member and surrounding the two-dimensional array of ultrasound transducers and defining a space proximate to the two-dimensional array; a full-matrix capture probe interface device communicatively coupled to the ultrasound probe, wherein the probe interface device is configured to sequentially activate each of the ultrasound transducers and to receive data corresponding to ultrasonic waves captured by each of the ultrasound transducers; and an ultrasound capture system communicatively coupled to the full-matrix capture probe interface device, wherein the ultrasound capture system receives data corresponding to the ultrasonic waves captured by each of the ultrasound transducers from the full-matrix capture probe interface device and generates an image of a surface based on the received data. In some embodiments, the ultrasound capture system generates an image of a surface and subsurface anatomy.

This summary is provided to introduce a selection of concepts in a simplified form that are further described below in the detailed description. This summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

FIG. 13 illustrates a step in an example sequence of ultrasound pulse emissions from the transducers of the transducer array of FIG. 4.

FIG. 14 illustrates another step in the example sequence of ultrasound pulse emissions of FIG. 13

FIG. 15 illustrates another step in the example sequence of ultrasound pulse emissions of FIG. 13

FIG. 16 illustrates another step in the example sequence of ultrasound pulse emissions of FIG. 13

FIG. 17 illustrates a step in another example sequence of ultrasound pulse emissions from the transducers of the transducer array of FIG. 4.

FIG. 18 illustrates another step in the example sequence of ultrasound pulse emissions of FIG. 17

DETAILED DESCRIPTION

Figure 1:
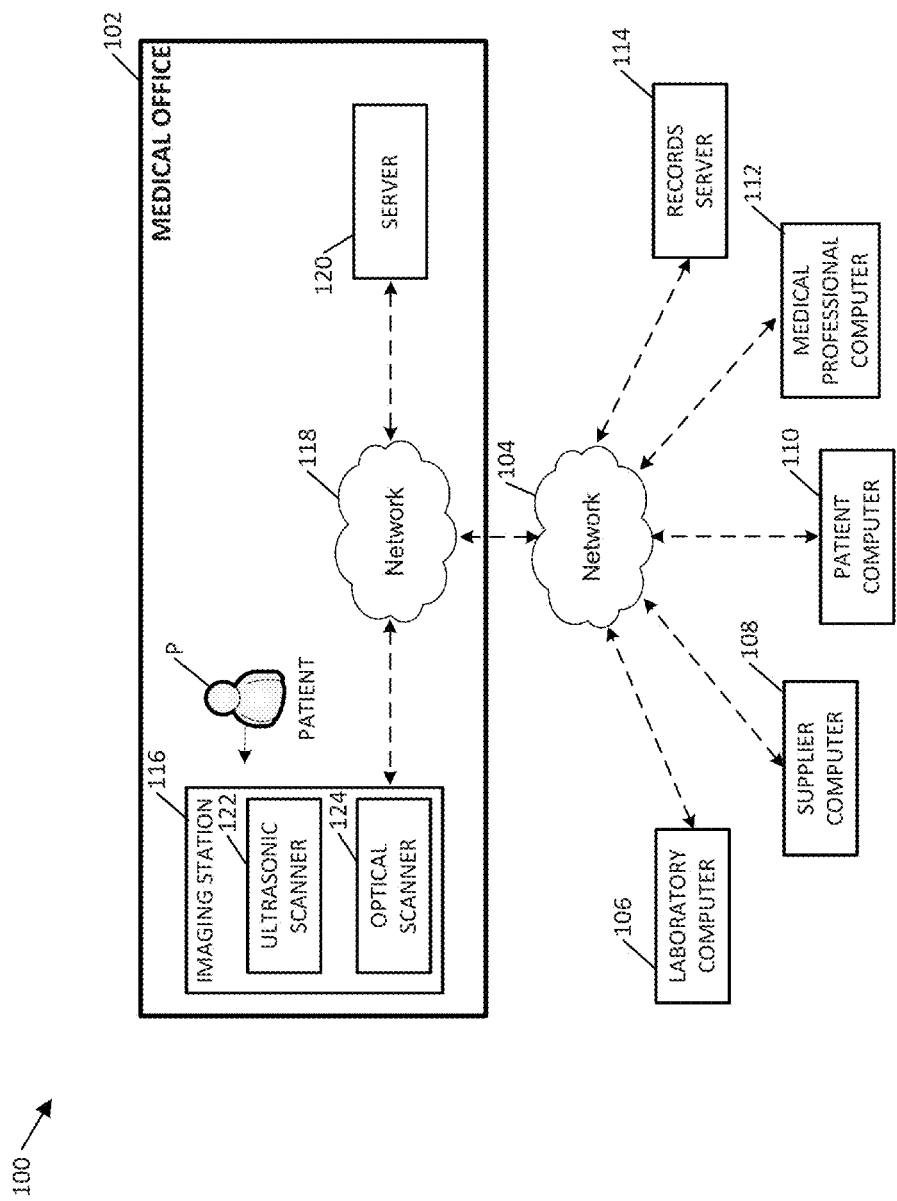
FIG. 1 is a schematic block diagram illustrating an example of a system 100 for ultrasound imaging of anatomy.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a schematic block diagram illustrating an example of a system 100 for ultrasound imaging of anatomy. In this example, the system 100 includes a medical office 102, a network 104, a laboratory computer 106, a supplier computer 108, a patient computer 110, a medical professional computer 112, and a records server 114.

The example medical office 102 includes an imaging station 116, a network 118, and a server 120. Examples of the medical office 102 include dental offices and physician's offices. Additionally, in at least some embodiments, the imaging station 116 is not located in a medical office. For example, in some embodiments, the imaging station 116 is configured to be used by a patient in his or her home. Additionally, in some embodiments, the imaging station 116 is configured to be used in a kiosk, such as might be found at a drug store, grocery store, or similar location. In yet other embodiments, the imaging station 116 may be located at a dental supplier such as a dental lab and may be configured for scanning of impressions for digital records and rapid prototyping of molds and prosthetics. In some of these embodiments, the imaging station 116 may transmit images or data back to a medical office 102. Additionally, the imaging station may be disposed in the medical office 102 or any other location and be configured to scan and transmit either impressions or dental models (e.g., which may be poured from an impression). The impression or dental model may be disposed in a bath of water or another ultrasound transmission medium to facilitate imaging. The imaging station may also be used to image dental restorations to identify internal features that may affect the longevity of the restoration such as bubbles and cracks (which may show as unexpected surfaces within a three-dimension image of a restoration). Restorations may be images before or after being placed in the oral cavity (e.g., to evaluate placement of the restoration within the patient's mouth and to determine when to replace an existing restoration before a failure occurs).

The example imaging station 116 operates to capture an image of the anatomy of the patient P. The imaging station 116 includes an ultrasonic scanner 122. The ultrasonic scanner 122 is a device that operates to generate images of patient anatomy using ultrasound pulses. In alternate embodiments, the ultrasonic scanner 122 operates to collect data that is than transmitted (such as over one or both of network 104 and network 118) to a computing device for image generation. The ultrasonic scanner is illustrated and described in greater detail herein, including in FIGS. 3-20. In at least some embodiments, the imaging station 116 operates to capture three-dimensional images of the craniofacial anatomy of the patient P. Non-limiting examples of the craniofacial anatomy of the patient P include the patient's dentition, gum tissue, mandible, maxilla, throat/airway, and temporomandibular joint. Additionally, at least some embodiments of the imaging station 116 include an optical scanner 124. Examples of optical scanners include laser scanners and parallax scanners. In these embodiments, the three-dimensional images may be generated by combing data captured with the ultrasonic scanner 122 and the optical scanner 124. However, some embodiments do not include the optical scanner 124.

The generated image of the anatomy of the patient P may be stored at the imaging station 116 or it may be transmitted across the network 118. In some embodiments, the image is transmitted to the server 120. In addition to images that show the three-dimensional shape of the anatomy, the images can include any format of descriptive data relating to the anatomy such as chemical characteristics of regions of the anatomy. Other embodiments are possible as well.

The network 118 communicates digital data between the imaging station 116 and the server 120. The network 118 may communicate data between additional devices as well. The network 118 can be a local area network or a wide area network, such as the Internet. The imaging station 116 and the server 120 can be in the same geographic location or can be in different locations.

The server 120 is a computing device. In some embodiments, the server 120 operates to receive images of the patient anatomy and to store those images. Additionally, the server 120 may associate the images with patient data such as biographical information and information about the circumstances under which the image was captured (e.g., location, time, equipment used, notes, procedures being performed or to be performed, etc.). Additionally, in some embodiments, the server 120 may operate to provide access to the images to other computers. For example, in some embodiments, the server 120 may include a web server that generates a web interface through which patients, colleagues, etc. may access some or all of the images.

The network 104 communicates digital data between one or more computing devices, such as the computing devices comprising the imaging station 116, the server 120, the laboratory computer 106, the supplier computer 108, the patient computer 110, the medical professional computer 112, and the records server 114. The network 104 can be a local area network or a wide area network, such as the Internet. In at least some embodiments, the network 118 and the network 104 are a single network, such as the Internet or the same local area network.

The laboratory computer 106 is a computing device and operates to perform various applications for a laboratory that provides services to the medical office 102. Examples of the laboratory include dental and orthodontic laboratories that operate to provide custom-fabricated components (e.g., crowns, bridges, other dental restorations, implants, splints, mouth guards, bracket placement jigs, brackets, etc.) for the medical office 102. In at least some embodiments, the laboratory computer 106 receives three-dimensional images of patient anatomy that are captured using the imaging station. In some examples, the laboratory computer 106 includes CAD applications that operate to design custom-fabricated components using the three-dimensional image data received from the imaging station 116. Once designed using the CAD applications, the custom-fabricated components may be physically modeled using rapid prototyping technologies. Additionally, in some embodiments, the laboratory computer 106 operates to generate a physical model from the received three-dimensional image data. The physical model may also be generated using rapid prototyping technologies, for example.

The supplier computer 108 is a computing device and operates to perform various applications for a supplier that provides supplies to the medical office 102. In some embodiments, the supplier computer 108 receives image or other data generated by the imaging station 116. In some embodiments, the information received by the supplier computer 108 does not include patient identifiable information. The supplier computer 108 may use these images or other data to determine a quantity or dimension of various supplies that may be needed at the medical office 102.

The patient computer 110 is a computing device and operates to perform various applications for a patient P of the medical office 102. In some embodiments, the patient computer 110 operates to receive three-dimensional images of the patient's anatomy. The three-dimensional images may be transmitted to the patient computer 110 by the server 120 or by the imaging station 116. In some embodiments, the three-dimensional images may include annotations from a medical professional. In addition, the patient computer 110 may also receive information about diagnoses, treatment plans, effectiveness of treatments, and mapping trends as a function of patient behavior and as a function of treatment applied. Other embodiments include additional information as well.

The medical professional computer 112 is a computing device and operates to perform various applications for a medical professional involved in the treatment of the patient P. Examples of medical professionals include dentists, physicians, and others who provide medical, dental, or healthcare services to patients. In some embodiments, the medical professional computer 112 operates to receive three-dimensional images of the patient's anatomy. Additionally, in some embodiments, the medical professional computer 112 operates to generate a user interface for measuring and annotating features of the patient's anatomy using the three-dimensional images. The medical professional computer may also be configured to use the three-dimensional images to generate components to be produced using rapid prototyping technology. Additionally, in some embodiments, the medical professional computer 112 provides an interface for communicating with colleagues such as a referring or consulting medical professional about the patient's physical anatomy and treatment options.

The records server 114 is a computing device and operates to store patient records. In some embodiments, the records server 114 may store the three-dimensional images captured using the imaging station 116. The records server 114 may include one or more relational databases or file systems.

Although the ultrasonic scanner 122 is disposed in the imaging station 116 of the medical office 102 in the embodiment of FIG. 1, the ultrasonic scanner 122 is not disposed in a medical office in other embodiments. For example, the ultrasonic scanner 122 may be portable and configured for use in an outdoor environment such as a forest or on a battlefield. Additionally, the ultrasonic scanner 122 may be configured to be transported and used in a mobile environment such as on a ship, plane, submarine, spaceship, or space station. The ultrasonic scanner 122 may also be configured for home use by the patient P.

Additionally, in some embodiments, the imaging station 116 may communicate with a computing device of an insurance provider for various purposes, such as to provide justification for a treatment or for other purposes. Alternatively, one or more of the laboratory computer 106, supplier computer 108, medical professional computer 112, and records server 114 may transmit the images or other data generated by the imaging station 116 to the computing device of an insurance provider. The imaging station 116 may also transmit the images or other data to a national practitioner databank or system for providing patient access to the images or other data.

Figure 2:
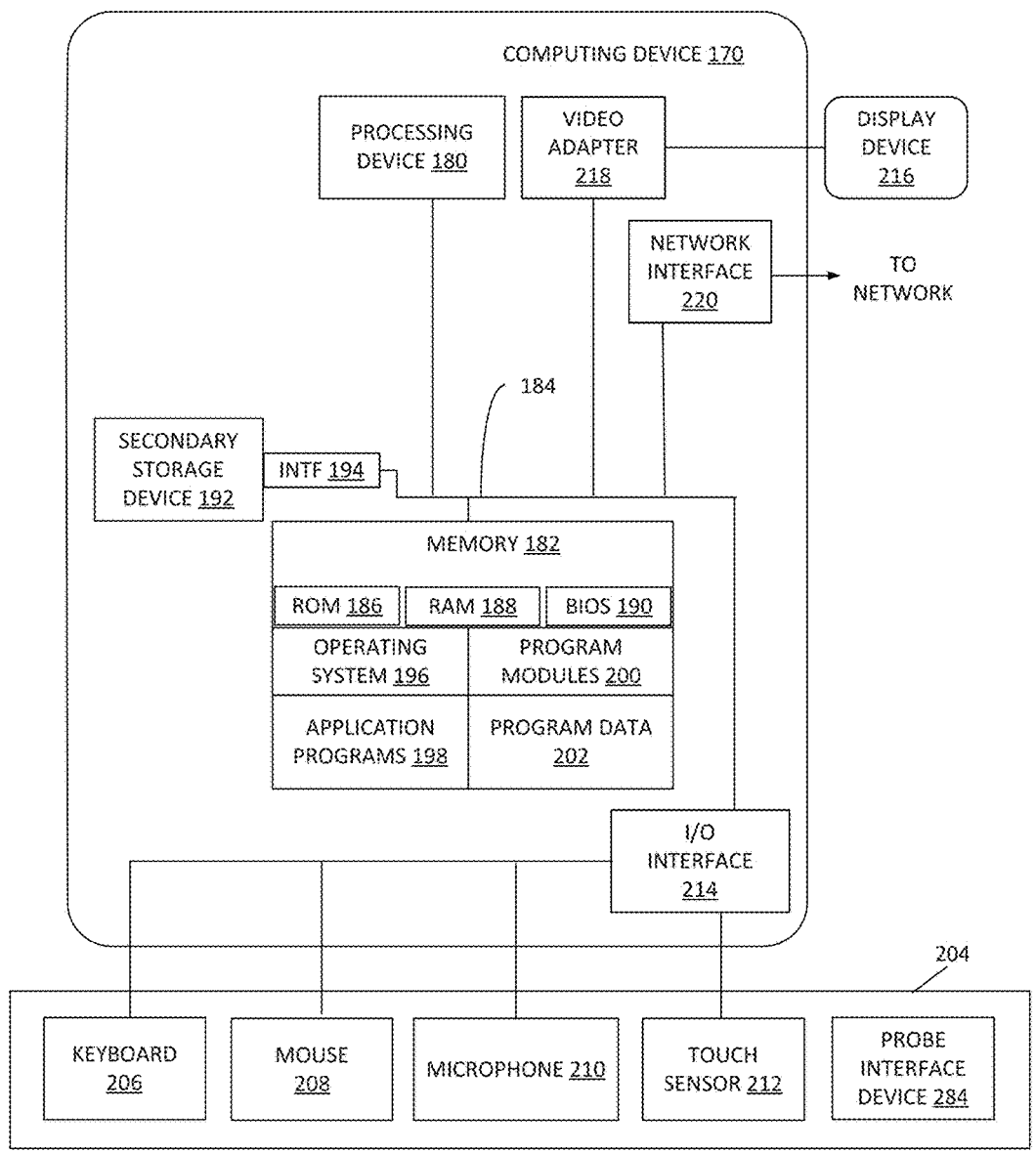
FIG. 2 illustrates an example architecture of a computing device, which can be used to implement aspects according to the present disclosure.

FIG. 2 illustrates an exemplary architecture of a computing device 170 that can be used to implement aspects of the present disclosure, including any of the plurality of computing devices described herein, such as the computing devices comprising the imaging station 116, the server 120, the laboratory computer 106, the supplier computer 108, the patient computer 110, the medical professional computer 112, the records server 114, the ultrasound capture system 286 (illustrated and described at least with respect to FIG. 3), and any other computing devices that may be utilized in the various possible embodiments.

The computing device illustrated in FIG. 2 can be used to execute the operating system, application programs, and software modules (including the software engines) described herein.

The computing device 170 includes, in some embodiments, at least one processing device 180, such as a central processing unit (CPU). A variety of processing devices are available from a variety of manufacturers, for example, Intel or Advanced Micro Devices. In this example, the computing device 170 also includes a system memory 182, and a system bus 184 that couples various system components including the system memory 182 to the processing device 180. The system bus 184 is one of any number of types of bus structures including a memory bus, or memory controller; a peripheral bus; and a local bus using any of a variety of bus architectures.

Examples of computing devices suitable for the computing device 170 include a desktop computer, a laptop computer, a tablet computer, a mobile computing device (such as a smart phone, an iPod® or iPad® mobile digital device, or other mobile devices), or other devices configured to process digital instructions.

The system memory 182 includes read only memory 186 and random access memory 188. A basic input/output system 190 containing the basic routines that act to transfer information within computing device 170, such as during start up, is typically stored in the read only memory 186.

The computing device 170 also includes a secondary storage device 192 in some embodiments, such as a hard disk drive, for storing digital data. The secondary storage device 192 is connected to the system bus 184 by a secondary storage interface 194. The secondary storage devices 192 and their associated computer readable media provide nonvolatile storage of computer readable instructions (including application programs and program modules), data structures, and other data for the computing device 170.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 192 or system memory 182, including an operating system 196, one or more application programs 198, other program modules 200 (such as the software engines described herein), and program data 202. The computing device 170 can utilize any suitable operating system, such as Microsoft Windows™, Google Chrome™ OS, Apple OS, Unix, or Linux and variants and any other operating system suitable for a computing device. Other examples can include Microsoft, Google, or Apple operating systems, or any other suitable operating system used in tablet computing devices.

In some embodiments, a user provides inputs to the computing device 170 through one or more input devices 204. Examples of input devices 204 include a keyboard 206, mouse 208, microphone 210, touch sensor 212 (such as a touchpad or touch sensitive display), and the probe interface device 284 (illustrated and described at least with respect to FIG. 3). Other embodiments include other input devices 204. The input devices are often connected to the processing device 180 through an input/output interface 214 that is coupled to the system bus 184. These input devices 204 can be connected by any number of input/output interfaces, such as a parallel port, serial port, game port, or a universal serial bus. Wireless communication between input devices and the interface 214 is possible as well, and includes infrared, BLUETOOTH® wireless technology, 802.11a/b/g/n, cellular, ultra-wideband (UWB), ZigBee, or other radio frequency communication systems in some possible embodiments.

In this example embodiment, a display device 216, such as a monitor, liquid crystal display device, projector, or touch sensitive display device, is also connected to the system bus 184 via an interface, such as a video adapter 218. In addition to the display device 216, the computing device 170 can include various other peripheral devices (not shown), such as speakers or a printer.

When used in a local area networking environment or a wide area networking environment (such as the Internet), the computing device 170 is typically connected to the network through a network interface 220, such as an Ethernet interface. Other possible embodiments use other communication devices. For example, some embodiments of the computing device 170 include a modem for communicating across the network.

The computing device 170 typically includes at least some form of computer readable media. Computer readable media includes any available media that can be accessed by the computing device 170. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 170.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 2 is also an example of programmable electronics, which may include one or more such computing devices, and when multiple computing devices are included, such computing devices can be coupled together with a suitable data communication network so as to collectively perform the various functions, methods, or operations disclosed herein.

Figure 3:
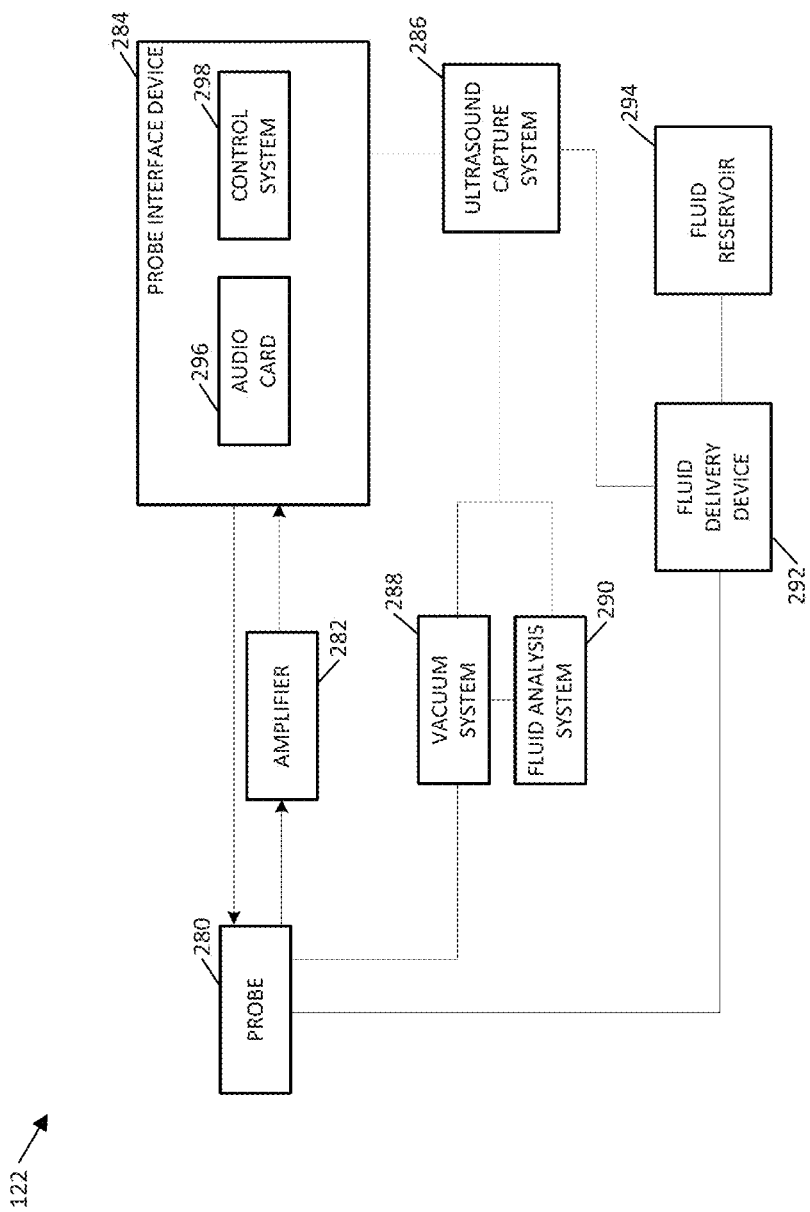
FIG. 3 is a schematic block diagram of an embodiment of the ultrasonic scanner of FIG. 1.

FIG. 3 is a schematic block diagram of an embodiment of the ultrasonic scanner 122. The ultrasonic scanner 122 includes a probe 280, an amplifier 282, a probe interface device 284, an ultrasound capture system 286, a vacuum system 288, a fluid analysis system 290, a fluid delivery device 292, and a fluid reservoir 294. However, not all embodiments of the ultrasonic scanner 122 include all of the components illustrated in FIG. 3. For example, some embodiments do not include the fluid analysis system 290. As another example, other embodiments do not include one or both of the vacuum system 288 and the fluid delivery device 292.

The probe 280 is a device that operates to generate ultrasonic waves and to capture reflected ultrasonic waves. In some embodiments, the probe 280 is configured to image a particular portion of the patient's anatomy, such as the craniofacial anatomy and, more particularly, the oral cavity. Further, some embodiments are configured to image the hard tissues (e.g., teeth, bones) of the oral cavity. In these embodiments, the ultrasonic waves penetrate the soft tissues (e.g., gums) before being reflected by the hard tissues. Embodiments of the probe 280 are described in greater detail elsewhere herein. Additionally, some embodiments capture both soft tissues and hard tissues. In this manner, the volume of the soft tissue can be determined, to for example evaluate and diagnosis periodontal conditions such as gum disease. In some embodiments, the soft tissues may be imaged using ultrasonic pulses having different properties than the ultrasonic pulses that are used for imaging hard tissues. In other embodiments, the soft tissue is imaged using a different technology such as optical imaging technology, which is then aligned with an image of the hard tissue.

The amplifier 282 is a device that receives one or more input signals and generates one or more amplified output signals. The amplifier 282 is configured to receive a signal corresponding to ultrasonic waves captured by the probe 280. In some embodiments, the amplifier 282 uniformly amplifies the received signal. Alternatively, the amplifier 282 may operate to apply a non-uniform amplification to the received signal. For example, in some embodiments, the amplifier 282 operates to amplify certain arrival times of signals more than others or to amplify signals differently based on the angle required for a given rectangular transducer. Additionally, the amplifier 282 may also include one or more filters that operate to process the received signal. For example, some embodiments of the amplifier 282 include one or more of a low-pass filter, a high-pass filter, and a band-pass filter.

The probe interface device 284 operates to send excitation signals to the probe 280 as well as to receive signals from the probe 280. In some embodiments, the probe interface device includes an ultrasound card 296 and control system 298. The ultrasound card 296 is a device that operates to generate ultrasound signals for transmission to the probe 280. In at least some embodiments, the ultrasound card 296 generates and transmits a plurality of ultrasound signals, such as an ultrasound signal for each transducer in the probe 280. In some embodiments, the transmission is a phased array arrangement using multiple transmitting transducers simultaneously, while other embodiments use a full-matrix capture approach, transmitting on a single transducer at a time, while receiving on multiple transducers.

The control system 298 operates to control the ultrasound card 296, to receive signals from the amplifier 282, and to communicate with the ultrasound capture system 286. In some embodiments, the control system 298 comprises a computing device. Alternatively, the control system 298 comprises an electronic circuit. Other embodiments are possible as well.

In addition to transmitting audio signals, some embodiments of the probe interface device 284 transmit additional signals to the probe 280 such as one or more control signals. For example, in at least some embodiments, the probe interface device transmits signals to control one or more status lights on the probe 280. Additionally, in some embodiments, the probe interface device 284 transmits a signal to the probe 280 that instructs the probe 280 to generate or capture ultrasound waves. Additionally, the probe interface operates to receive signals representing user inputs received on the probe 280, such as via a button, switch, or other user-actuable input device. In at least some embodiments, the user inputs control one or more of the following parameters excitation pulse, amplifier gain, filters, and timing of excitation pulses.

The ultrasound capture system 286 is a computing device and communicates with the probe interface device 284. In some embodiments, the ultrasound capture system 286 communicates with the probe interface device 284 to control the probe 280 and to received data from the probe 280. Additionally, the ultrasound capture system 286 may also communicate with one or more of the vacuum system 288 and the fluid delivery device 292. In some embodiments, the ultrasound capture system 286 and the probe interface device 284 are combined into a single device.

The vacuum system 288 is a device that operates to generate a vacuum so as to collect fluids. In some embodiments, the vacuum system 288 is in fluid communication with the probe 280 to create a vacuum at or near the portion of the patient's anatomy that is being imaged. For example, the vacuum system 288 may collect fluid from between the probe 280 and the portion of the patient's anatomy being imaged. The vacuum system 288 may be connected to the probe 280 with flexible tubing. The flexible tubing may be formed from plastic, latex, rubber, or another material. In some embodiments, the vacuum system 288 is not connected to the probe 280. Instead, the vacuum system 288 may be independent of the probe 280 such that an operator may direct a tube connected to the vacuum system 288 separately from the probe 280 to for example collect fluid at a different location than the probe 280.

In some embodiments, the vacuum system 288 is configured to direct collected fluids to a drain or a waste receptacle. In other embodiments, the vacuum system 288 is configured to direct the collected fluids (or at least a portion thereof) to the fluid analysis system 290.

In some embodiments, the fluid analysis system 290 is a device that operates to detect the presence of one or more substances in a sample of the fluid collected by the vacuum system 288. For example, the fluid analysis system 290 may operate to detect the presence of bacteria (or particular types of bacteria), bacterial byproducts, fungus (or particular types of fungus), fungal byproducts, other types of microorganisms, chemicals, proteins, sugars, and other types of substances. The fluid analysis system 290 may include one or more of a flow cytometer, a mass spectrometer, or other technology to analyze the fluid sample. In addition to detecting the presence of substances within the fluid, some embodiments also determine the quantity or concentration of various substances that are detected in the fluid.

In some embodiments, the fluid analysis system 290 communicates with the ultrasound capture system 286. For example, the fluid analysis system 290 may transmit a signal to the ultrasound capture system 286 representing data that identifies the substances that were detected in a fluid sample. The data may identify one or both of the concentration and quantity of the various substances detected in the fluid sample as well. Additionally, the fluid analysis system 290 may correlate the data with the location where the fluid sample was connected. The data may also be correlated with various clinical conditions or procedural information (e.g., the type of procedure that is being performed, medical/dental history for the patient, etc.).

In some embodiments, the fluid analysis system 290 receives signals from the ultrasound capture system 286 that represent various instructions. The example instructions may instruct the fluid analysis system 290 to begin analyzing a sample, capture a sample of a particular size for analysis, or stop analyzing samples. Other embodiments are possible as well.

The fluid delivery device 292 is a device that operates to deliver one or more fluids such as water. In some embodiments, the fluid delivery device 292 is connected to the probe 280 and delivers one or more fluids to the probe 280. A fluid pump is an example of the fluid delivery device 292. However, other embodiments are possible as well.

In some embodiments, the fluid delivery device 292 is connected to the probe 280 with flexible tubing. The flexible tubing may be formed from plastic, latex, rubber, or another material. However, in some embodiments, the fluid delivery device 292 is not connected to the probe 280. Instead, the fluid delivery device 292 may be independent of the probe 280 such that an operator may direct a tube connected to the fluid delivery device 292 separately from the probe 280 to, for example, deliver fluid to a different location than the probe 280.

In some embodiments, the fluid delivery device 292 is connected to a fluid reservoir 294 and delivers the fluid stored therein. In other embodiments, the fluid delivery device 292 is connected to other fluid sources, such as a water line or tap. Additionally, some embodiments of the fluid delivery device 292 are connected to multiple sources of fluids and operate to select between the sources or to mix the fluids received from the multiple sources.

The fluid reservoir 294 is a device that operates to store one or more fluids. The fluid reservoir 294 may be connected to the fluid delivery device 292 with flexible tubing such as tubing formed from rubber, plastic, latex, or another material. In some embodiments, the fluid reservoir 294 is a tank, which may or may not be pressurized.

Additionally, in some embodiments, the fluid delivery device 292 and the fluid reservoir are integral (e.g., the fluid delivery device 292 includes the fluid reservoir 294). Or in the case of a pressurized tank, the fluid reservoir 294 may be the fluid delivery device 292.

Although the embodiment shown in FIG. 3 includes one probe 280 and one probe interface device 284, other embodiments may include multiple probes and multiple probe interface devices. For example, in some embodiments a single ultrasound capture system 286 is configured to communicate with and control multiple probes and probe interface devices. For example, each dental chair in a dental office may include a probe and a probe interface device that connect (wired or wirelessly) to a single ultrasound capture system 286.

Figure 4:
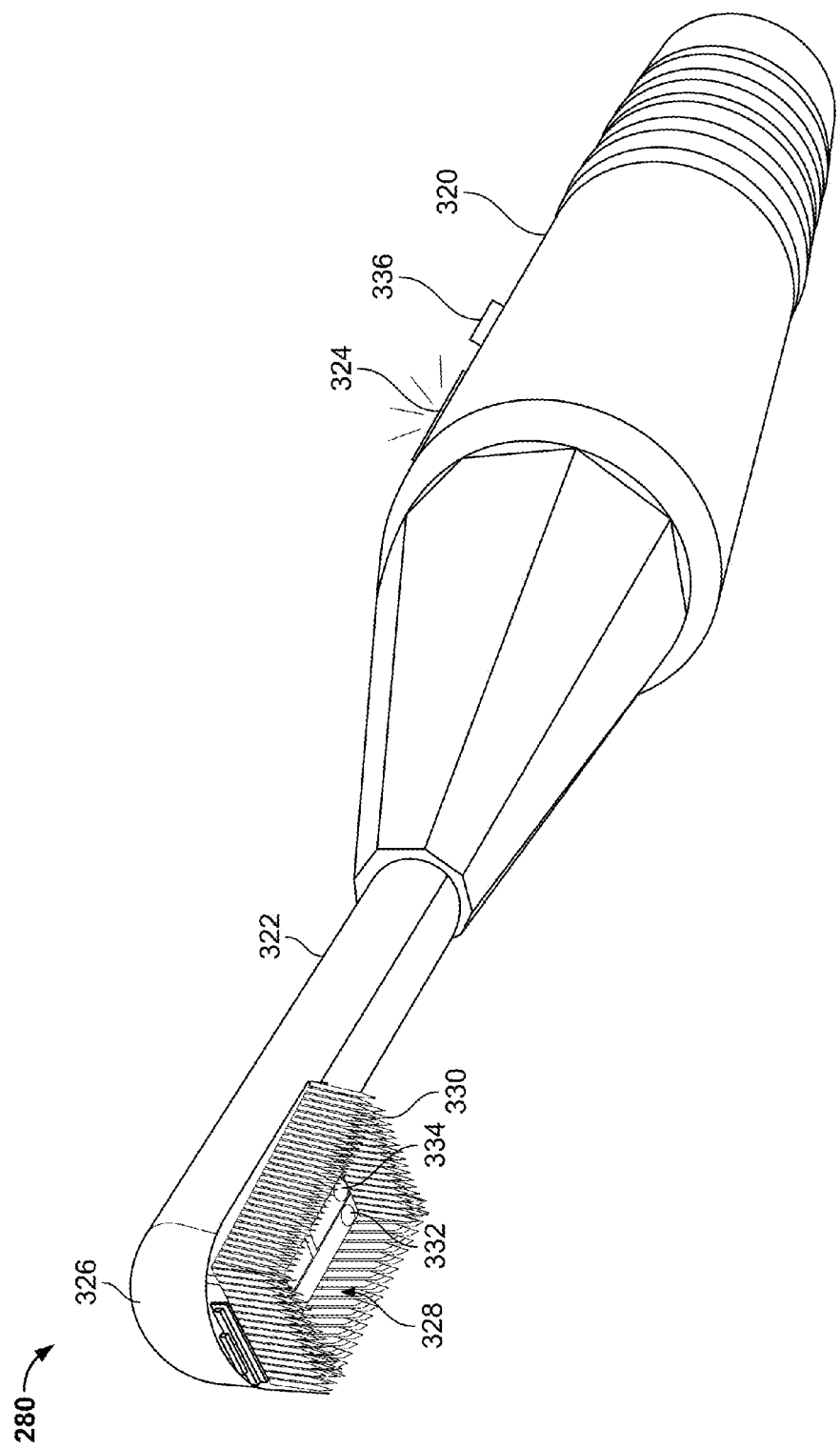
FIG. 4 illustrates an embodiment of the probe of FIG. 3.

FIG. 4 illustrates an embodiment of the probe 280. The probe 280 includes a handle 320 and an elongate member 322.

The handle 320 is a structure and may have a cylindrical form. In some embodiments, the handle 320 includes a communication device 324 and an input device 336. The handle may be formed to be held in the hand of an operator of the probe 280. For example, the handle 320 may have a cylindrical form with a diameter of between 0.25 and 2 inches. However, embodiments with other forms and other diameters are possible as well. Additionally, some embodiments include ridges or indentations to better fit the hand of an operator. The handle 320 may also include a cushioned outer layer to enhance the operator's comfort.

The communication device 324 operates to communicate information to the operator of the probe. For example, in some embodiments, the communication device comprises a light-emitting diode that lights up to convey information to the operator. In some embodiments, the light-emitting diode lights up when the probe is successfully collecting imaging data of the anatomy of the patient. In other embodiments, the light-emitting diode lights up to indicate that the probe is moving too fast to reliably collect imaging data. Some embodiments include additional light-emitting diodes. Alternatively or additionally, some embodiments include display panels as well, such as a liquid-crystal display, a light-emitting diode display panel, or another type of display panel. Other embodiments are possible as well.

The input device 336 may comprise one or more buttons, switches, knobs, and other user-actuable input devices. In at least some embodiments, the input device 336 is configured to receive inputs from a user to activate and deactivate imaging functions performed by the probe. Additionally, the input device 336 may also be configured to control various parameters of the probe such as excitation pulse, amplifier gain, filters, and timing of excitation pulses. In at least some of these embodiments, a signal corresponding to the input received from a user via the input device 336 is transmitted to the probe interface device 284.

The elongate member 322 is a structure and is coupled to the handle 320. The elongate member 322 includes a tip 326, a transducer array 328, a sheath 330, a fluid dispensing tube 332, and a suction tube 334. The elongate member 322 is configured to extend out from the handle 320 to the tip 326. Beneficially, the operator of the probe 280 may position the tip 326 near the anatomy of the patient that the operator wishes to image. For example, some embodiments of the elongate member 322 are configured to allow the tip 326 to be inserted into and maneuvered within the oral cavity (i.e., the mouth) of a patient. The elongate member 322 may have a cylindrical form and a diameter of between 0.5 and 1 inches. However, other embodiments have other forms (such as, for example, an oval or rectangular cross-section) and other diameters. Embodiments of the tip 326 are shown and described in greater detail with respect to FIG. 23.

In at least some embodiments, the transducer array 328 is disposed at or near the tip 326. The transducer array 328 is a device that operates to emit and detect (or capture) ultrasound waves. Embodiments of the transducer array 328 are illustrated and described in greater detail with respect to FIGS. 5-8.

In at least some embodiments, the sheath 330 is disposed around the transducer array 328. The sheath 330 operates to maintain the imaging field of the transducer array 328. For example, in some embodiments the sheath 330 traps fluid between the transducer array 328 and the anatomy of the patient, improving the transmission of the ultrasound waves emitted by the transducer array 328 and reflected by the anatomy.

In at least some embodiments, the sheath 330 may be formed from a plurality of discrete flexible bristles that surround the transducer array and defines a space for fluid. The flexible bristles may be formed from plastic, rubber, silicone, latex, or another material. Alternatively, in at least some other embodiments, the sheath 330 may be formed from a sheet (or curtain) of a flexible material such as plastic, rubber, silicone, latex, or another material. Beneficially, in embodiments where the sheath 330 is formed from a flexible material, the sheath 330 may adapt to and remain in contact with nonuniform surfaces of the anatomy being imaged. Additionally, in some embodiments, the sheath 330 is formed to have a non nonuniform durometer. For example, the sheath 330 may have a lower durometer (and thus greater flexibility) near the transducer array 328 than elsewhere. Other embodiments are possible as well.

In some embodiments, the sheath 330 is integral with the elongate member 322. In other embodiments, the sheath 330 is a separate component that is removably coupled to the elongate member 322. Further, the sheath 330 may be a disposable component formed from a disposable material that is used with one patient. Beneficially, the disposable embodiments of the sheath 330 may simplify the process of cleaning and sterilization of the probe 280 between patients.

In some embodiments, the fluid dispensing tube 332 is disposed within the space defined by the sheath 330. In some embodiments, the fluid dispensing tube 332 operates to dispense a fluid such as water into the space defined by the sheath 330.

In some embodiments, the suction tube 334 is disposed outside of but near the sheath 330. In this manner, the suction tube 334 pulls the fluid dispensed by the fluid dispensing tube 332 through and out of the space defined by the sheath 330. In at least some embodiments, the suction tube 334 is integral with the sheath 330. For example, the sheath 330 may be formed from a plurality of bristles, some of which may be hollow tubes that are connected to the vacuum system 288. Other embodiments are possible as well.

Figure 5:
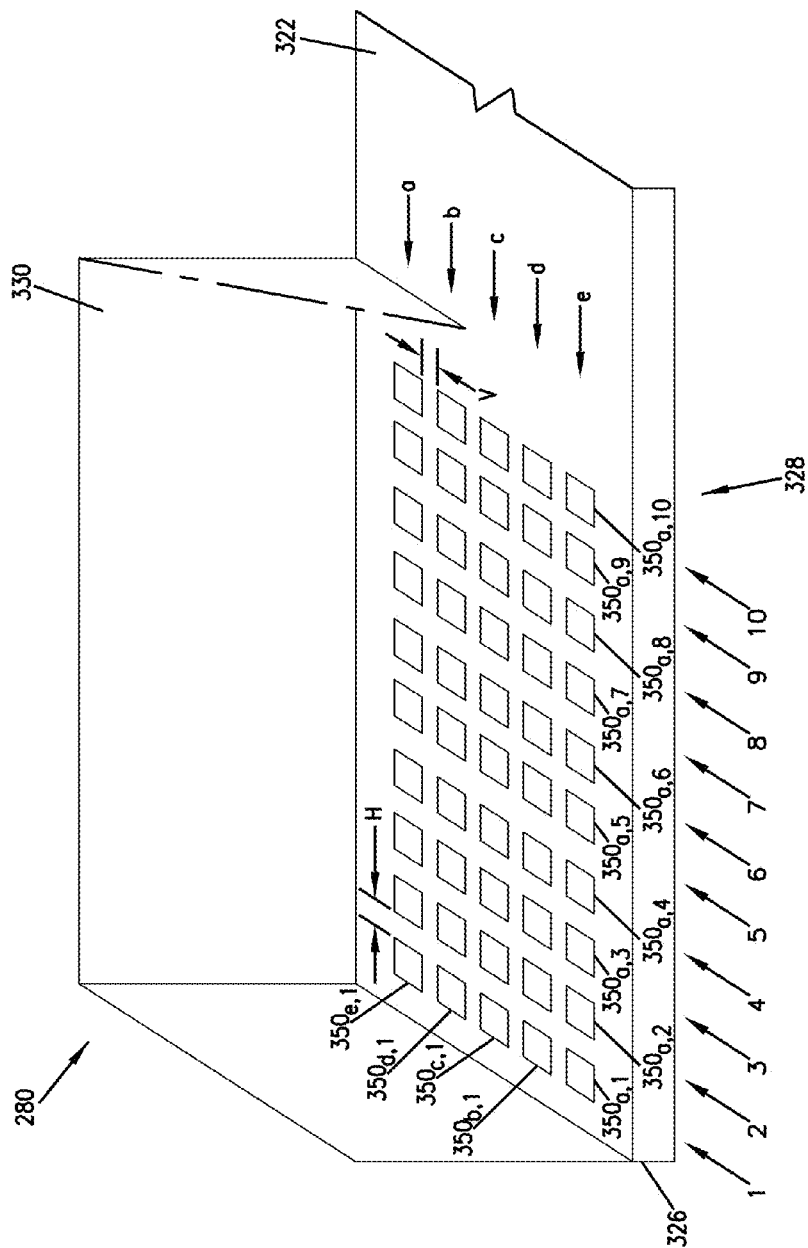
FIG. 5 illustrates a close-up view of and embodiment of the tip of the probe of FIG. 3.

FIG. 5 illustrates a close-up view of an embodiment of the tip 326 of the probe 280, including the elongate member 322 and the transducer array 328. Also shown is a cut-away view of the sheath 330. The transducer array 328 comprises an m×n array of transducers (referred to collectively as transducers 350). In the embodiment shown in FIG. 5, the transducers are arranged in a 5×10 array, with the rows being labeled with the letters a-e and the columns being labeled with the numbers 1-10. Thus, each individual transducer of the transducers 350 can be identified by a combination of a letter and a number. For example, a transducer $350_{a,1}$ is disposed in the lower-left corner in this example. Other embodiments having different dimensions for the m×n array of transducers are possible as well. Further, in some embodiments m and n are equal.

In some embodiments, the transducers 350 are piezoelectric elements that vibrate when actuated in a manner that emits ultrasound waves. For example, in some embodiments, the transducers 350 vibrate (and emit ultrasound waves) at a frequency in the range of 5-10 Mhz. Other embodiments vibrate (and emit ultrasound waves) at a frequency that is higher or lower, such as in a range of 1-50 Mhz. Other embodiments of the transducers 350 are possible however. In some embodiments, the each of the transducers 350 comprises a square surface having dimensions between 0.0157-0.0394 inches squared (0.4-1.0 mm squared). Other embodiments with other dimensions are possible however. Beneficially, when the transducers 350 comprise square surfaces, the ultrasound waves produced by the transducers 350 expand evenly in all directions as the ultrasound wave propagates away from the transducers 350 (i.e., the beam spread of the ultrasound wave is uniform). However, other embodiments of the transducers 350 comprise surfaces that are not square as well.

In various embodiments, the transducer array 328 may have various sizes. For example, in at least one embodiment, the transducer array 328 has a width of 1 inch and a height of 0.5 inches. However, other embodiments have different dimensions. In some embodiments, the transducers 350 are separated from each other by a distance H in the horizontal direction, and a distance V in the vertical direction. In at least some embodiments, the distances H and V are greater than the width and height of the individual transducers 350. For example, in at least some embodiments, the distance H and V are between 0.07-0.12 inches. Other embodiments are possible however. Various considerations regarding to the spacing of the transducers 350 in the transducer array are illustrated and described with respect to the embodiment illustrated in FIG. 6-7.

Figure 6:
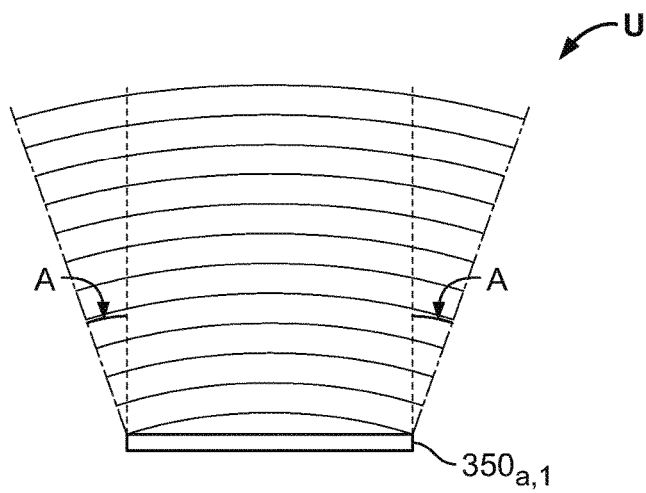
FIG. 6 illustrates an embodiment of a transducer of FIG. 5 emitting an ultrasound pulse.

FIG. 6 illustrates an embodiment of the transducer $350_{a,1}$ emitting an ultrasound pulse (or wave) U. In this example, the ultrasound pulse U is shown expanding by a beam spread angle A in both directions as it propagates away from the transducer $350_{a,1}$. Many factors may affect the beam spread angle A, such as the shape and size of the transducer. In at least some embodiments, the beam spread angle A is between 20-30 degrees.

Figure 7:
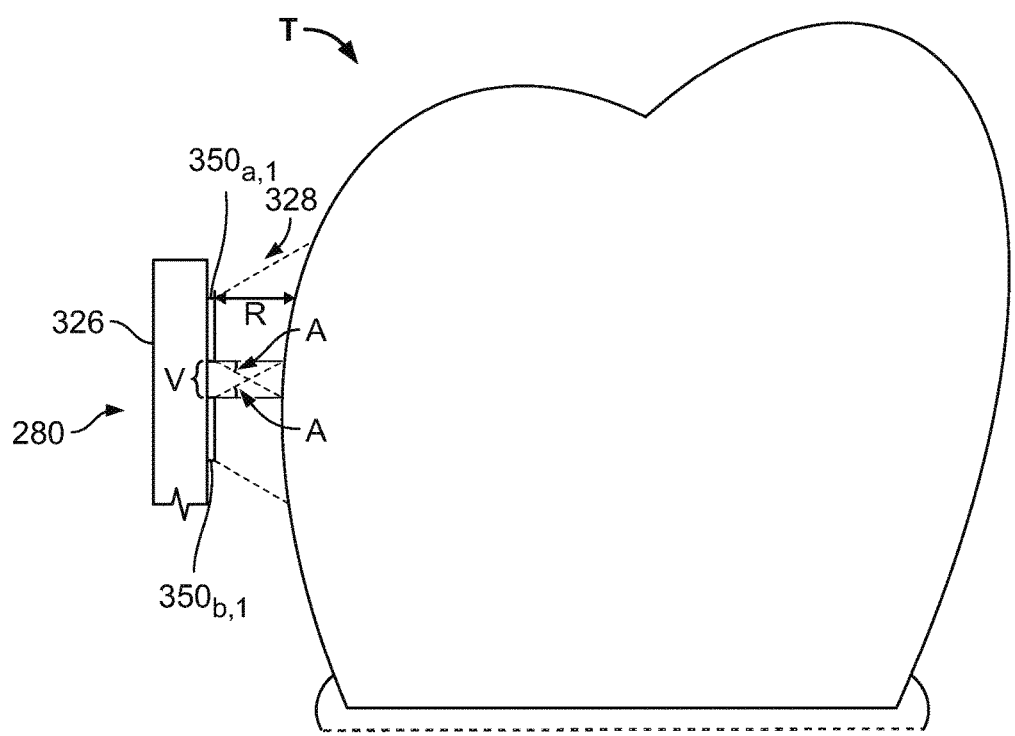
FIG. 7 is a profile view of an embodiment of the probe of FIG. 3 operating to image patient anatomy in a dental environment.

FIG. 7 is a profile view of an embodiment of probe 280 operating to image patient anatomy in a dental environment. More particularly, FIG. 7 illustrates the tip 326 of the probe 280 and the transducers $350_{a,1}$ and $350_{b,1}$ of the transducer array 328. In this example, the tip 326 is disposed so that the surfaces of the transducers 350 are approximately parallel to a tooth T that is being imaged. Additionally, the tip 326 is disposed so that the transducers $350_{a,1}$ and $350_{b,1}$ are disposed at a distance R away from the tooth T, where R is within an operating range of the probe 280. The operating range of the probe 280 is based on the beam spread of the ultrasound waves produced by the transducers and is defined so that the ultrasound waves of adjacent transducers within transducer array 328 overlap. The overlapping ultrasound waves operate to minimize or eliminate gaps in imaging the surface of the tooth T. In other words, the operating range can be selected such that the expansion by the beam spread angle A of the ultrasound wave produced by $350_{a,1}$ is greater than half of the distance V between the adjacent transducers. In some embodiments, the operating range is 0.16" to 0.5". However other embodiments are possible that operate in different ranges based at least in part on the arrangement of transducers in the transducer array 328.

Figure 8:
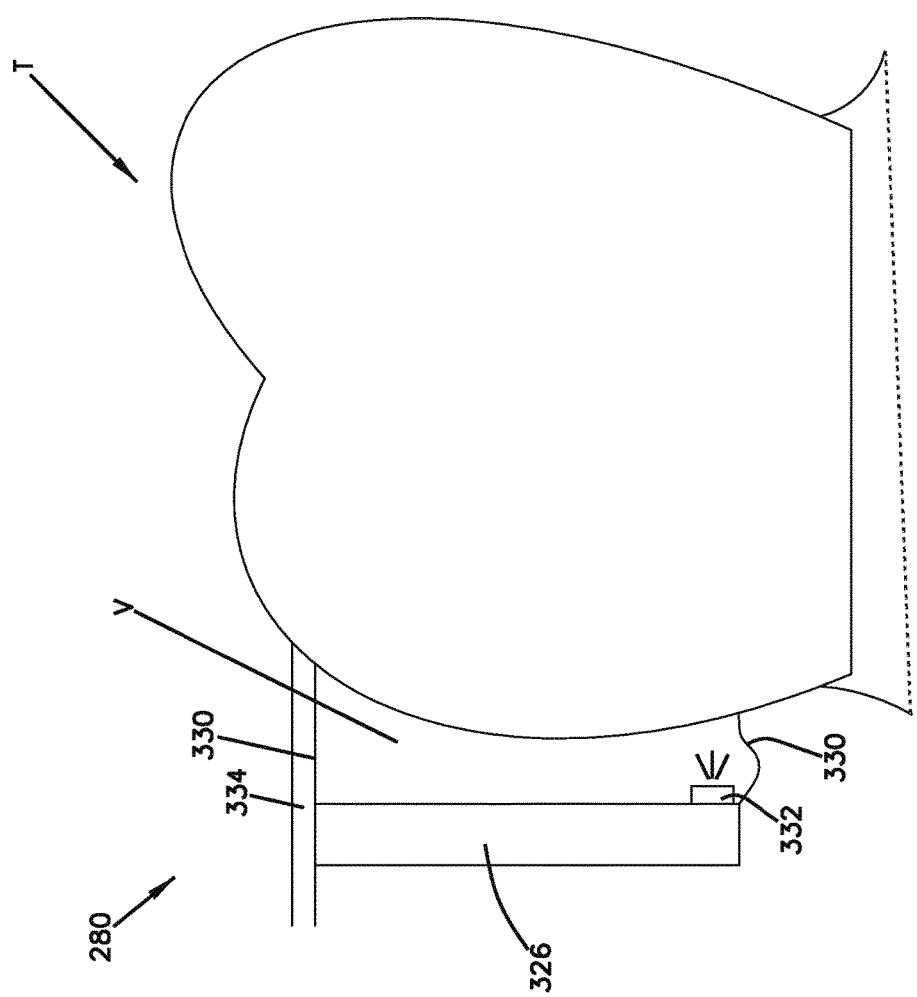
FIG. 8 is another profile view of an embodiment of the probe of FIG. 3 operating to image patient anatomy in a dental environment.

FIG. 8 is another profile view of an embodiment of probe 280 operating to image patient anatomy in a dental environment. More particularly, FIG. 8 illustrates how the sheath 330 operates to enclose a volume V. In some embodiments, the fluid dispensing tube 332 dispenses fluid into the volume V and fills the volume V with fluid. Beneficially, the fluid may allow for improved propagation of the ultrasound waves emitted by the transducer array 328 and reflected by the tooth T.

Figure 9:
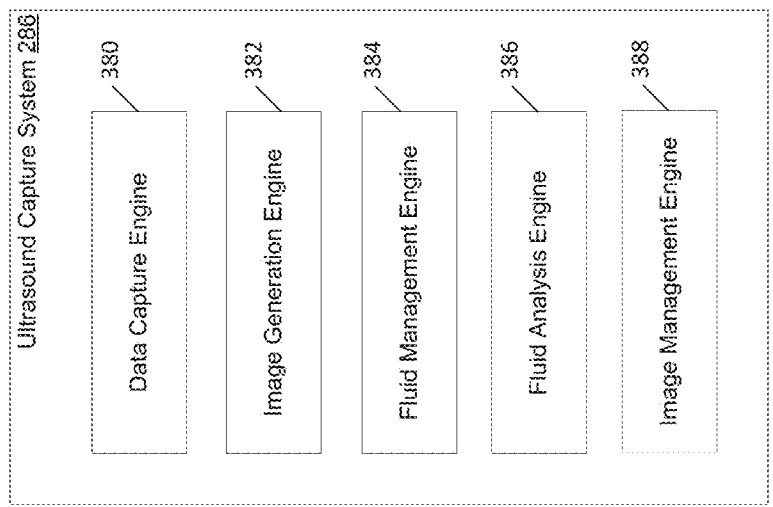
FIG. 9 illustrates a schematic block diagram of an embodiment of the ultrasound capture system of FIG. 3.

FIG. 9 illustrates a schematic block diagram of an embodiment of the ultrasound capture system 286. In this example, the ultrasound capture system 286 includes a data capture engine 380, an image generation engine 382, a fluid management engine 384, a fluid analysis engine 386, and an image management engine 388. Other embodiments are possible that include fewer, additional, or different engines as well.

The data capture engine 380 operates to control the probe interface device 284, the operation of the probe 280 and, more specifically, the transducers 350 of the transducer array 328. In at least some embodiments, the data capture engine 380 directs the transducers 350 to perform full-matrix capture ultrasound imaging, which is described in greater detail elsewhere herein.

The image generation engine 382 operates to process the data captured using the probe 280 to generate images of the patient P's anatomy. In some embodiments, the image generation engine 382 operates to generate three-dimensional images.

The fluid management engine 384 operates to control the delivery and removal of fluid to the probe 280 so as to maintain a usable field for ultrasound imaging.

The fluid analysis engine 386 operates to process data related to the analysis of fluid retrieved from the field by, for example, the vacuum system 288. In at least some embodiments, the fluid analysis engine 386 operates to associate fluid analysis data from the fluid analysis system 290 with positions in images of the patient P's anatomy such as images generated using the image generation engine 382.

The image management engine 388 operates to manage the images generated by the ultrasonic scanner 122. In at least some embodiments, the image management engine 388 associates images generated by the ultrasonic scanner 122 with one or more of bibliographic, medical, dental, diagnostic, and treatment information for the patient P. Some embodiments of the image management engine 388 operate to store the images, and some embodiments operate to transmit the images.

Figure 10:
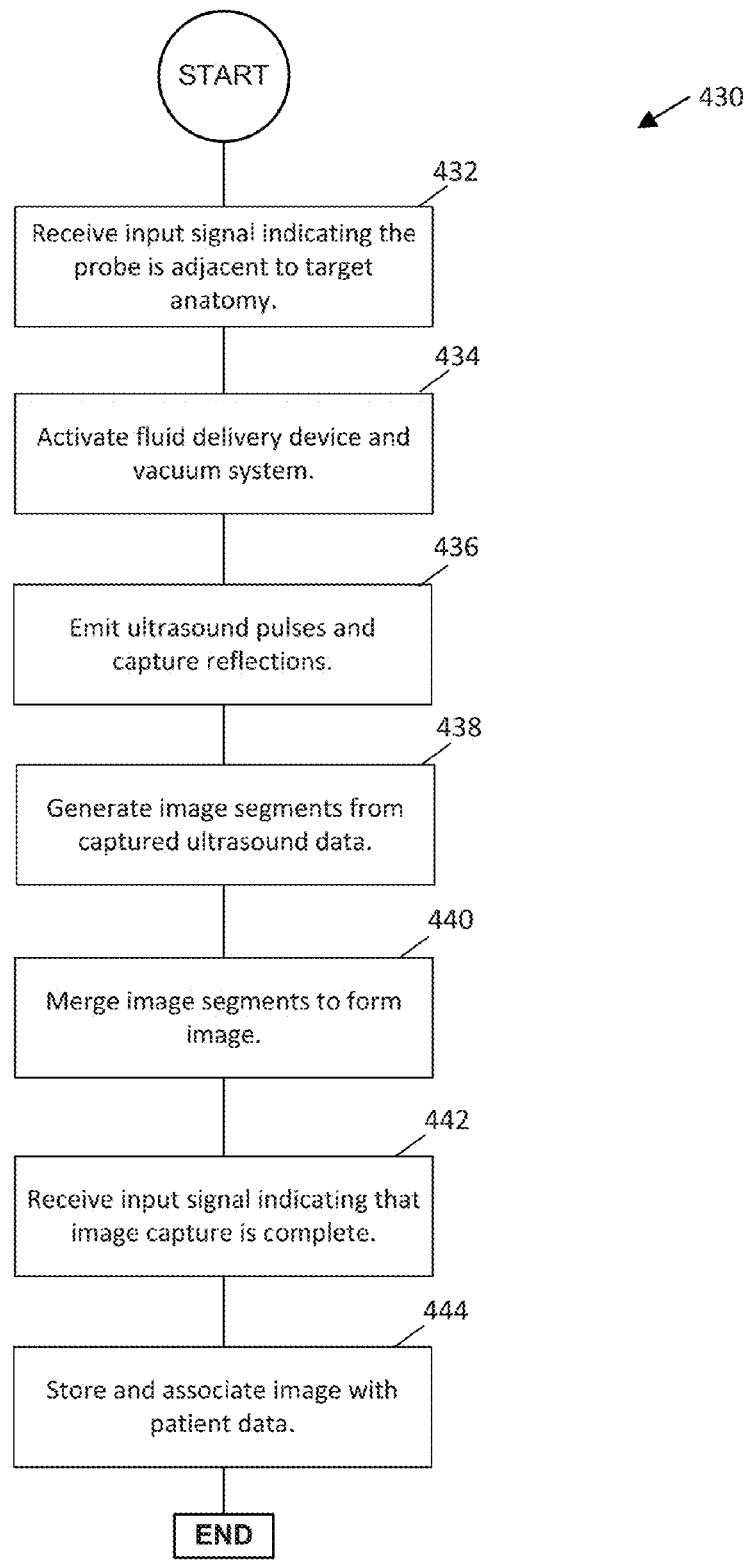
FIG. 10 is a flow chart illustrating an example method of capturing patient anatomy data using the ultrasonic scanner of FIG. 1.

FIG. 10 is a flow chart illustrating an example method 430 of capturing patient anatomy data using the ultrasonic scanner 122. In some embodiments, the method 430 is performed by the ultrasound capture system 286 in conjunction with one or more processing devices (such as the central processing unit 180, shown in FIG. 2). In this example, the method 430 includes operations 432, 434, 436, 438, 440, 442, and 444, which are discussed below in numeric order but, in at least some embodiments, are performed in a different order.

At operation 432, an input signal is received to indicate that probe 280 is adjacent to the target patient anatomy and that the operator is ready for imaging to begin. The input may be received via a switch or other type of user-actuatable input disposed on the probe. Alternatively, the operator may generate the input signal using one of the user inputs 240 of the ultrasound capture system 286.

At operation 434, the fluid delivery device 292 and the vacuum system 288 are activated. In some embodiments, the fluid management engine 384 transmits an electronic activation signal to one or both of the fluid delivery device 292 and the vacuum system 288. However, in other embodiments the fluid delivery device 292 and the vacuum system are manually controlled by an operator. In these embodiments, the operator may actuate a lever, switch, or other type of user-actuatable input on the fluid delivery device 292 and the vacuum system 288 to activate each of them. Additionally, once activated, the rate of fluid delivery and the strength of the vacuum may be adjusted by the fluid management engine 384 or manually by the operator. In at least some embodiments, the rate of fluid delivery and the strength of the vacuum are set so as to maintain a volume of fluid in the space defined by the sheath 330. Beneficially, the volume of fluid maintained in the sheath facilitates the transmission of the emitted and reflected ultrasonic waves.

At operation 436, ultrasound pulses are emitted by the transducers 350 of the transducer array 328. In at least some embodiments, the ultrasound pulses are emitted in multiple iterations, which can be used to generated an image segment (or snapshot) for each iteration. An iteration may comprise sequentially activating each transducer of the transducers 350 to cause the activated transducer to emit an ultrasound pulse. In at least some embodiments, after a pulse is emitted by one of the transducers 350, there is a delay before the next ultrasound pulse is emitted to allow for the capture of ultrasound reflections with the transducer array 328. This process of emitting an ultrasound pulse with a transducer and capturing reflections with multiple transducers is referred to herein as full-matrix capture ultrasound imaging. In some embodiments of full-matrix capture ultrasound imaging, all of the transducers 350 of the transducer array 328 capture reflections of ultrasound pulses sequentially emitted by each of the transducers. Example methods of emitting ultrasound pulses and capturing reflections are illustrated and described with respect to FIG. 11.

At operation 438, image segments are generated from ultrasound signals captured by the transducer array 328, which correspond to reflections of emitted ultrasound pulses. Depending on the embodiment and the duration of imaging, multiple image segments may be generated based on the captured ultrasound signals. In at least some embodiments, an image segment is generated using the captured signals from a single iteration through the transducers 350. However, other embodiments are possible as well. For instance, an image segment may be generated using some of the signals captured during more than one iteration. Additionally, the ultrasound signals from a single iteration may be used to generate more than one image segment.

In at least some embodiments, a time of flight is calculated between the emission of the ultrasound pulse and the capture of its reflections. The time of flight is used along with the positions of the emitting transducer and the receiving transducer of the transducers 350 to determine a potential point (i.e., spatial position) on the patient anatomy that reflected the pulse. Because multiple transducers may capture a reflection of an emitted ultrasound pulse, a single emitted ultrasound pulse may result in multiple potential points on the patient anatomy. An image segment may be generated using a plurality of determined potential positions. For example, an image segment may be generated using the points determined from each of the transducers 350 emitting one ultrasound pulse. The image segment may correspond to a surface or region of the patient anatomy that has approximately the same dimensions as the transducer array. Example methods of generating an image segment are illustrated and described with respect to FIG. 19.

Additionally, in some embodiments, the generated image segment is associated with fluid analysis data produced by the fluid analysis system 290. For example, in some embodiments, one or more of a list of detected substances and a list of determined substance concentrations in the fluid analyzed by the fluid analysis system 290 is associated with an image segment. In some embodiments, various procedures are used to identify the correct fluid analysis data to associate with an image segment so that the fluid analysis data corresponds to fluid that was captured from the same portion of the patient's anatomy that is represented by the image segment. In some embodiments, the image segment is associated with the fluid analysis data calculated for fluid that reaches the fluid analysis system 290 a predetermined time period after the ultrasound signals used to generate the image segments were captured. This predetermined time period may correspond to the time required for the collected fluid to travel to the fluid analysis system 290.

At operation 440, the image segments are merged together to form an image. Since the probe 280 is moving during capture of the ultrasound signals, the image segments will capture different portions of the patient's anatomy. And sequentially captured image segments will represent adjacent portions of the patient's anatomy. Furthermore, if the rate of capturing image segments is faster than the rate at which the probe moves, the sequentially captured image segments will represent overlapping portions of adjacent patient anatomy.

In some embodiments, the image segments are aligned by identifying the overlapping portions of sequentially captured image segments and then aligning those overlapping portions to one another. Repeating this process, each image segment can be merged into an image using the overlapping portion for alignment. In some embodiments, the image segments are merged into an image as they are generated during the scanning process. Beneficially, by merging the image segments while the probe is being used to scan the patient's anatomy, the ultrasound capture system 286 may warn the operator of the probe 280 that the image segment could not be merged and that the probe 280 is, for example, being moved too fast.

Additionally, in some embodiments, the image is displayed (e.g., using display device 216) as it is being generated. Various embodiments use various techniques to display the image. For example, the image may be displayed as a point cloud, a polygonal mesh, or using any other technique for representing images. Beneficially, by displaying the image, the operator can view imaging progress and is better able to determine when scanning is complete. In at least some embodiments, the image displayed during scanning is of a lower quality than the final image that is stored. For example, the image displayed during scanning may include outlier data points that will later be filtered out or corrected. Alternatively, in some embodiments, only a portion of the captured data points are displayed during scanning. As another alternative, the image segments may be displayed rather than the merged image.

At operation 442, an input signal is received to indicate that imaging is complete. Like the input received at operation 432, this input may be received via a switch other type of user-actuatable input disposed on the probe. Alternatively, the operator may generate the input signal using one of the user inputs 240 of the ultrasound capture system 286.

At operation 444, the image is stored and associated with patient data. In some embodiments, the image data is stored as the captured data points. In other embodiments, the image is converted to another format such as a polygonal mesh. The image can be converted using various techniques known in the art to convert a cloud of data points into a polygonal mesh (e.g., but not limited to, using a shrink-wrap meshing technique). Additionally, in some embodiments, the polygonal mesh may be decimated to remove redundant data and allow for more efficient storage.

In some embodiments, patient data such as biographical information (e.g., but not limited to, patient name, age, gender, etc.) is associated with the image. Alternatively, the image may be associated with information about the circumstances under which the image was captured but that does not necessarily identify the patient. This may be useful for purposes of collecting anonymous data for a clinical study or in collecting images for the purposes of identifying a patient (or body) based on the imaged anatomy.

Figure 11:
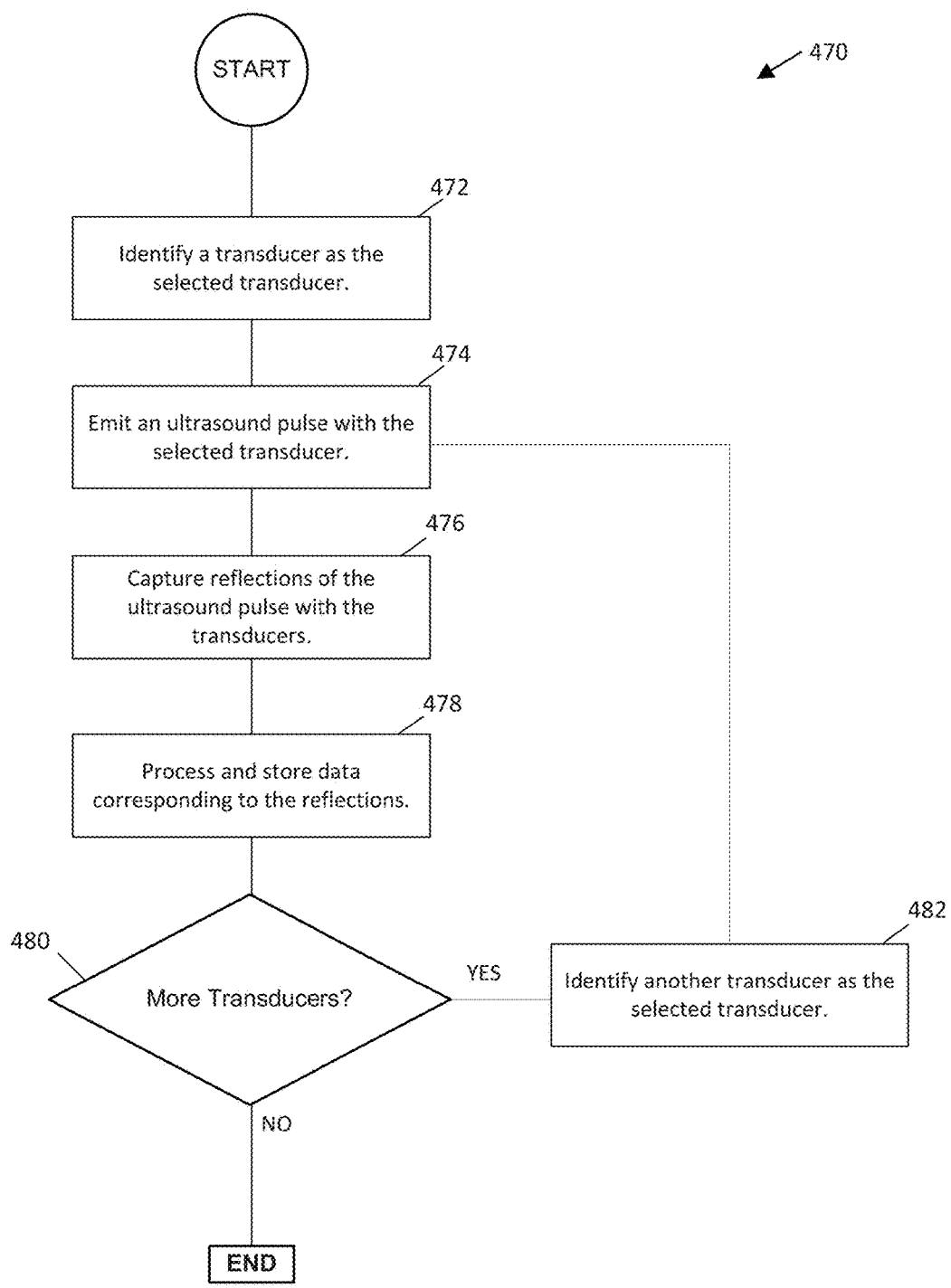
FIG. 11 is a flow chart illustrating an example method of performing an iteration of ultrasound capture using the ultrasonic scanner of FIG. 1.

FIG. 11 is a flow chart illustrating an example method 470 of performing an iteration of ultrasound capture using the ultrasonic scanner 122. In some embodiments, the method 470 is performed by the data capture engine 380 in conjunction with one or more processing devices (such as the central processing unit 180, shown in FIG. 2). In this example, the method 470 includes operations 472, 474, 476, 478, 480, and 482, which are discussed below in numeric order but, in at least some embodiments, are performed in a different order.

At operation 472, a transducer is identified and set as the selected transducer. The transducer is identified for purposed of iterating through the transducers 350 of the transducer array 328. In some embodiments, a transducer disposed in a particular location within the transducer array (e.g., upper-left corner, center, etc.) is identified. In other embodiments, a transducer is identified randomly from the transducers 350 in the transducer array 328. Other embodiments are possible as well.

At operation 474, the selected transducer emits an ultrasound pulse. In some embodiments, the selected transducer is activated by an electrical signal transmitted by the probe interface device 284. For example, in some embodiments, the probe interface device 284 operates to transmit an activation wave to the selected transducer. Example activation waves include impulse waves and square waves. Other wave forms may be used as well. In various embodiments, the activation wave has various voltage levels. For example, the peak voltage of the transmitted wave is 50 volts in some embodiments. In other embodiments, the peak voltage is between 25 and 200 volts. Examples of the activation waves and the received waves are illustrated and described with respect to FIG. 12.

At operation 476, the probe interface device 284 listens for received ultrasound reflections on at least some of the transducers 350. In some embodiments, the probe interface device 284 listens on all of the transducers 350. In other embodiments, the probe interface device 284 listens on a portion of the transducers that are disposed in a location that is likely to receive the reflected ultrasound wave. In some embodiments, the probe interface device listens for a predetermined listening time period. For example, in some embodiments, the predetermined listening time period is selected from the range 4-16 μs. Additionally, in some embodiments, the probe interface device 284 waits for a predetermined time period before beginning to listen for ultrasound reflections. Beneficially, by waiting, the probe interface device 284 minimizes the likelihood that residual ultrasound pulse energy remaining in the probe will be detected as a reflected ultrasound pulse. In some embodiments, the predetermined time period is between 5-10 μs. Other embodiments are possible as well.

At operation 478, the received reflections are processed and data corresponding to the reflections are stored. In some embodiments, a time of flight is calculated for at least some of the received ultrasound reflection on the various transducers. The time of flight is calculated by subtracting the time the ultrasound pulse was emitted from the time the ultrasound pulse was received.

In some embodiments, the signal corresponding to the reflection of the ultrasound pulse is subject to signal processing such as amplification (e.g., using the amplifier 282) and other signal processing techniques prior to determining the time of flight. For example, the received reflection may generate a signal with the shape of two periods of a sinusoidal wave. In some embodiments, the signal representing the reflection is rectified and subjected to a Hilbert transform to generate an envelope around the pulse. Using the processed signal, the leading edge of the pulse and the amplitude of the pulse can be determined. Additionally, in some embodiments, the pulse signal is subject to an amplitude threshold filter to eliminate noise.

In some embodiments, the time of flight information is stored with identifiers of the emitting transducer and the receiving transducer. Additionally, in some embodiments, the amplitude of the received ultrasound pulse is also stored. This information may then be used to determine the location or other characteristic of the patient's anatomy that reflected the ultrasound pulse.

At operation 480, it is determined whether there are additional transducers in the transducer array 328 that have not yet emitted an ultrasound pulse during the current iteration. If so, the method continues to operation 482. If not, the method ends.

At operation 482, a next transducer is identified as the selected transducer. The next transducer may be identified based on a location within the transducer array 328. For example, the next transducer may be the next transducer in a particular row or column of the transducer array 328. Alternatively, the next transducer may be selected based on a random order. Other embodiments are possible as well (e.g., skipping every other transducer, etc.). Additionally, in some embodiments, the method will wait for a second predetermined time period. Beneficially, by waiting for the second predetermined time period, the reflections of the previously emitted ultrasound wave have time to attenuate significantly. In some embodiments, the second predetermined time period is in the range of 50-1000 μs. After operation 482, the method returns to operation 474.

Once all of the transducers in the current iteration have emitted an ultrasound pulse and the method has ended, operation 438 (described with respect to FIG. 10) may be performed to generate an image. Beneficially, while the ultrasound capture system 286 is performing operation 438 to generate images, a new iteration of the method 470 may be initiated to continue to perform ultrasound capture. The ultrasound capture system 286 may wait a third predetermined amount of time to initiate a new iteration. The third predetermined period of time may be comparable to the second predetermined period of time, or it may be much longer. In one embodiment, the third predetermined period of time is one second. Although in the embodiment described in FIG. 11 only a single transducer is activated at a time, in some embodiments multiple transducers are activated simultaneously. Example embodiments of single transducers emitting pulses sequentially are illustrated and described with respect to FIGS. 13-16. Example embodiments of multiple transducers simultaneously emitting ultrasound pulses are shown in FIGS. 17-18.

Figure 12:
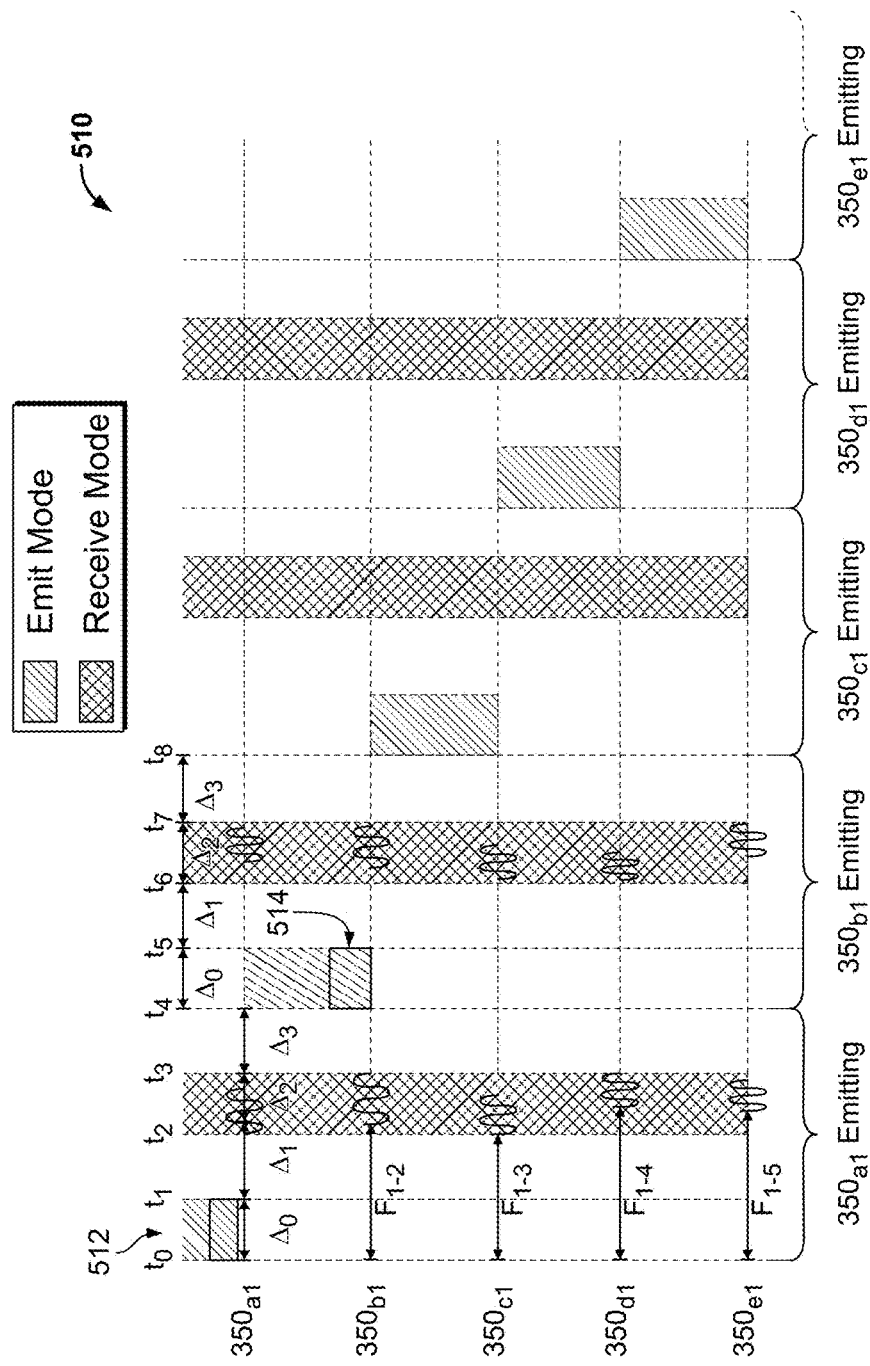
FIG. 12 illustrates a waveform graph representing example signals sent to and received from the various transducers of the transducer array of FIG. 4.

FIG. 12 illustrates a waveform graph 510 representing example signals sent to and received from the various transducers 350 of the transducer array 328. In FIG. 12, the waveforms of transducers $350_{a,1}$, $350_{b,1}$, $350_{c,1}$, $350_{d,1}$, and $350_{e,1}$ are shown. Between t0 and t1 an activation wave 512 is shown in the waveform of transducer $350_{a,1}$.

Between t1 and t2, the predetermined time period for waiting before listening for reflected waves is shown. Between t2 and t3, the probe interface device 284 listens for signals corresponding to reflections of the ultrasound pulses received at the transducers. In this example, the reflections of the ultrasound pulse generate a signal that has the form of two periods of a sinusoidal wave. As can be seen in FIG. 12 the reflection of the pulse reaches the various transducers at different times. These differences are a result of the difference in distance between the emitting and receiving transducers and the different distances to the location of the patient anatomy that reflects the pulse. Between t3 and t4, the second predetermined time period is shown. This time period allows for further attenuation of the reflections of the ultrasound pulse.

After the second predetermined time period, the process begins again with the transducer $350_{b,1}$ emitting an activation wave 514 of the ultrasound pulse. The pulse is emitted for the time period shown between t4 and t5. Then, a waiting period is shown between t5 and t6. Then between t6 and t7, the probe interface device listens for signals corresponding to the reflected ultrasound pulses. Then, another waiting period is shown between t7 and t8 before the process can begin again with the transducer $350_{c,1}$. This process continues until all of the transducers 350 in the transducer array 328 have emitted an ultrasound pulse.

FIGS. 13-16 schematically illustrate an example sequence of ultrasound pulse emissions from embodiments of the transducers 350 of the transducer array 328. In the embodiment shown in FIGS. 13-16 only one transducer emits an ultrasound pulse at a time. In FIG. 13, the transducer $350_{a,1}$ is shown emitting an ultrasound pulse. In FIG. 14, the transducer $350_{b,1}$ is shown emitting an ultrasound pulse. In FIG. 15, the transducer $350_{c,1}$ is shown emitting an ultrasound pulse. In FIG. 16, the transducer $350_{d,1}$ is shown emitting an ultrasound pulse. The sequence illustrated in FIGS. 13-16 is just an example and other embodiments emit ultrasound pulses according to different sequences.

FIGS. 17-18 schematically illustrate an example sequence of ultrasound pulse emissions from embodiments of the transducers 350 of the transducer array 328. In the embodiment shown in FIGS. 17-18 multiple transducers emits ultrasound pulses simultaneously. For example, two of the transducers 350 that are located in different regions of the transducer array 328 may emit ultrasound pulses simultaneously. In this embodiment, the probe interface device 284 listens for reflections of the ultrasound pulses on only a portion of the transducers 350, such as the portion of the transducers 350 that are likely to receive a reflection of the ultrasound pulse. Beneficially, these embodiments may allow for faster cycling through of the transducers 350 when it is not expected that the reflected ultrasound pulses will reach all of the transducers 350 in the transducer array 328.

In FIG. 17, the transducers $350_{a,1}$ and $350_{c,6}$ are shown emitting an ultrasound pulse simultaneously. Additionally, the transducers $350_{a,2}$, $350_{b,1}$, and $350_{b,2}$ are shown as receiving reflected ultrasound pulses. In this example, the transducers $350_{a,2}$, $350_{b,1}$, and $350_{b,2}$ are the only transducers that are expected to receive reflections of the ultrasound pulse emitted by the transducer $350_{a,1}$. Similarly, the transducers $350_{b,5}$, $350_{b,6}$, $350_{b,7}$, $350_{c,5}$, $350_{c,7}$, $350_{d,5}$, $350_{d,6}$, and $350_{d,7}$ are shown as receiving reflected ultrasound pulses and are the only transducers that are expected to receive reflections of the ultrasound pulse emitted by the transducer $350_{c,6}$.

FIG. 18 shows an example of the subsequent ultrasound emission in the iteration begun in FIG. 17. In FIG. 18, the transducers $350_{b,1}$ and $350_{d,6}$ are shown emitting an ultrasound pulse simultaneously. The transducers $350_{a,1}$, $350_{a,2}$, $350_{b,2}$, $350_{c,1}$, and $350_{c,2}$ are shown as receiving reflected ultrasound pulses and are the only transducers that are expected to receive reflections of the ultrasound pulse emitted by the transducer $350_{b,1}$. Similarly, the transducers $350_{c,5}$, $350_{c,6}$, $350_{c,7}$, $350_{d,5}$, $350_{d,7}$, $350_{e,5}$, $350_{e,6}$, and $350_{e,7}$ are shown as receiving reflected ultrasound pulses and are the only transducers that are expected to receive reflections of the ultrasound pulse emitted by the transducer $350_{d,6}$.

The illustrated sequence continues until all of the transducers 350 have emitted an ultrasound pulse. The sequence illustrated in FIGS. 17-18 is just an example and other embodiments emit ultrasound pulses according to different sequences. Additionally, in some embodiments more than two transducers emit ultrasound pulses simultaneously and larger or smaller portions of the transducer array 328 listen for reflections of the ultrasound pulses.

Figure 19:
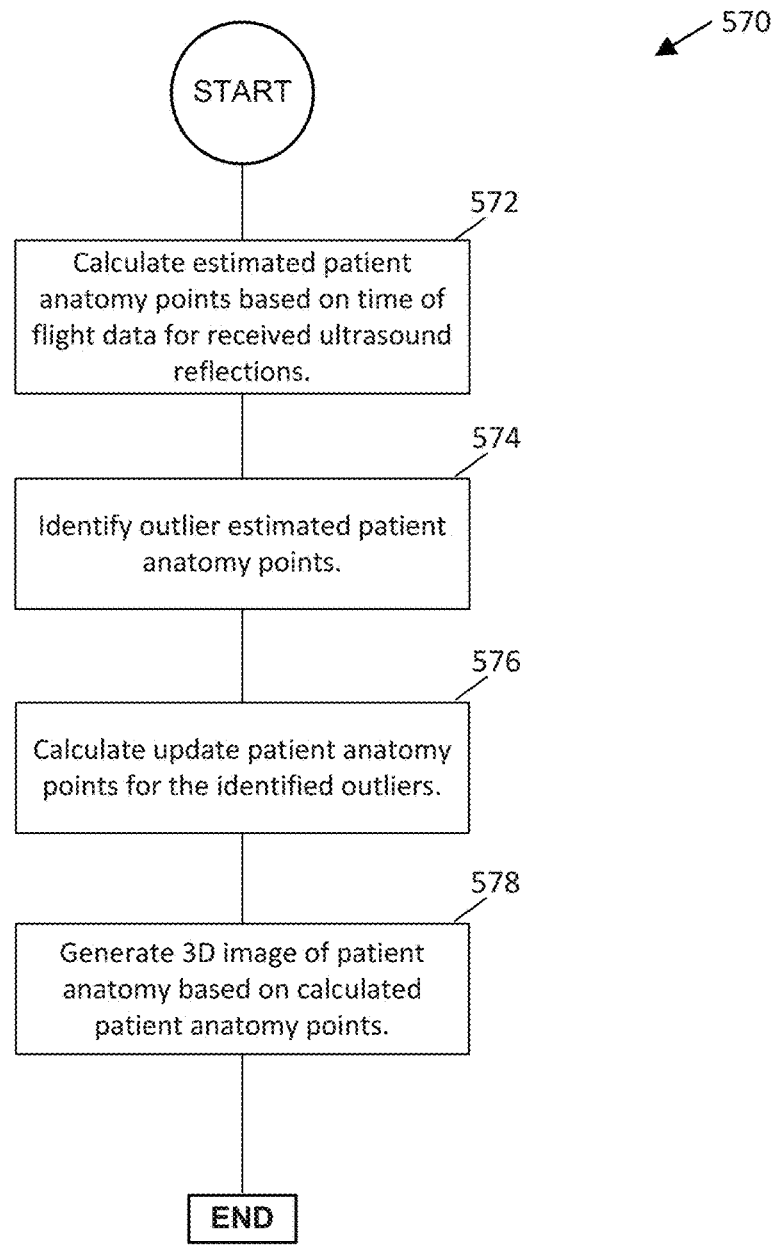
FIG. 19 is a flow chart illustrating an example method of generating an image using data captured using the ultrasonic scanner of FIG. 1.

FIG. 19 is a flow chart illustrating an example method 570 of generating an image using data corresponding to the reflections of ultrasound pulses captured using the ultrasonic scanner 122. In some embodiments, the method 570 is performed by the image generation engine 382 in conjunction with one or more processing devices (such as the central processing unit 180, shown in FIG. 2). In this example, the method 570 includes operations 572, 574, 576, and 578, which are discussed below in numeric order but, in at least some embodiments, are performed in a different order.

At operation 572, estimated patient anatomy points are calculated based on the captured time of flight information. In some embodiments, the estimated patient anatomy points are calculated for each time of flight data point by assuming that the estimated patient anatomy point is disposed at a location that projects onto the transducer array plane at the midpoint between the sending transducer and the receiving transducer. Using this assumption, the time of flight information is then used to calculate the vertical offset from the transducer array plane to the estimated patient anatomy point.

Figure 20:
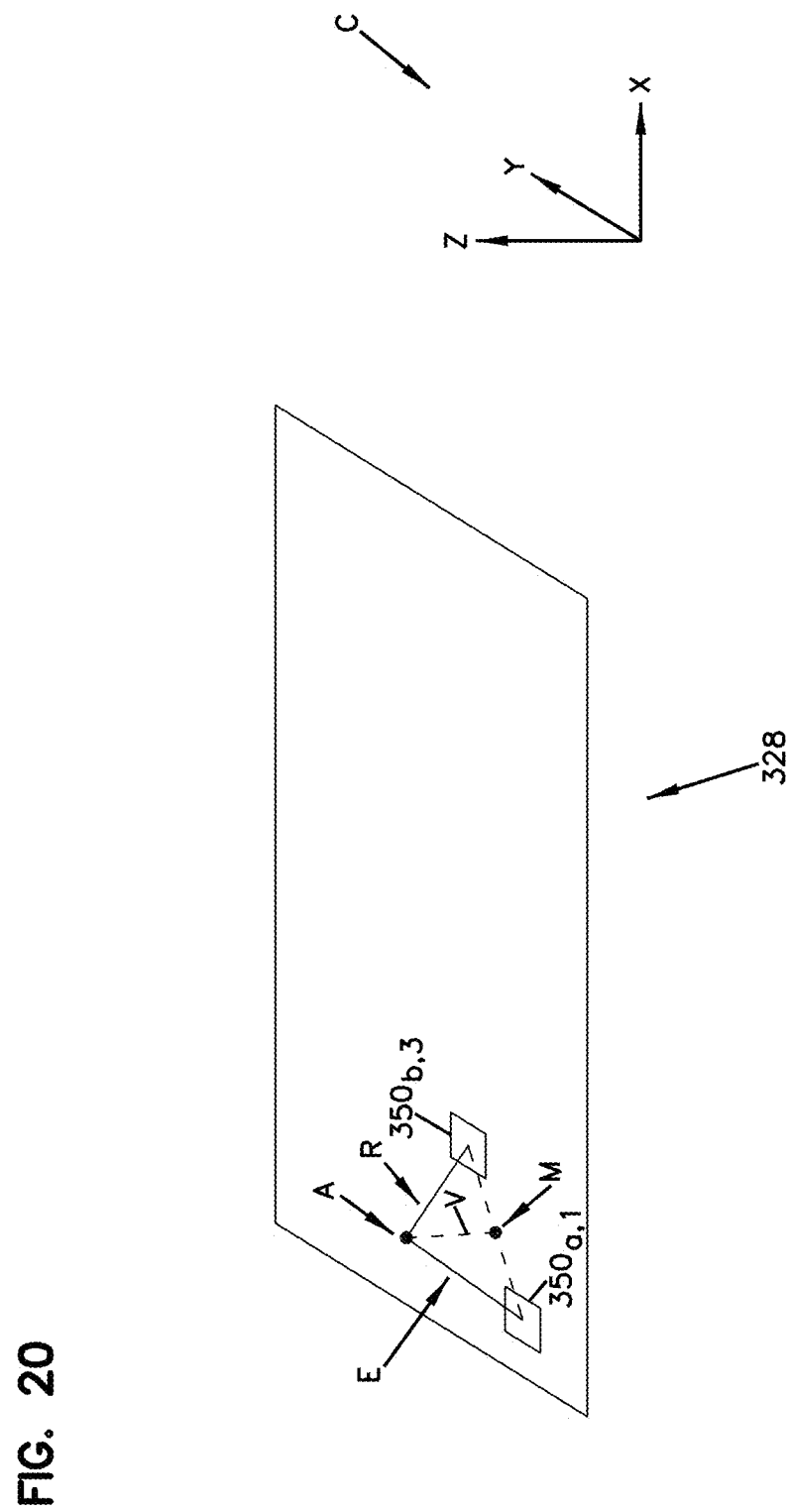
FIG. 20 illustrates an example of determining the location of an estimated patient anatomy point in accordance with embodiments of the method of FIG. 19.

FIG. 20 illustrates an example of determining the location of an estimated patient anatomy point A in accordance with operation 572 of some embodiments. In this illustration, a coordinate system C is shown. The x-axis and y-axis correspond to the surface of the transducer array 328 (i.e., the transducer array plane). The z-axis corresponds to a vertical offset from transducer array 328.

In this example, the estimated patient anatomy point A is determined from an ultrasound pulse emitted by the transducer $350_{a,1}$, the reflection of which is received by the transducer $350_{b,3}$. The x and y coordinates of the estimated patient anatomy point A are determined by calculating the midpoint M between the transducer $350_{a,1}$ and the transducer $350_{b,3}$. The z-coordinate is then calculated by determining a vertical offset V from the transducer array 328 based on the time of flight information. Specifically, the vertical offset V is selected so that the time for the ultrasound pulse to traverse a emission path E and a reflection path R is equal to the calculated time of flight. Time of flight can be converted to path distance and vice versa using the relationship between velocity, travel distance, and elapsed time.

Returning now to FIG. 19, at operation 574, the locations of the estimated patient anatomy points determined by operation 572 are analyzed to identify outliers. In some embodiments, an estimated patient anatomy point is identified as an outlier based on proximity to other estimated patient anatomy points. For example, an estimated patient anatomy point may be identified as an outlier if it is not within a predetermined distance (e.g., 10-100 µm) of a predetermined quantity (e.g., 2-5) of other estimated patient anatomy points. After outlier detection, in some embodiments, the estimated patient anatomy points that have not identified as outliers may be treated as determined patient anatomy points. Other embodiments use different or additional methods of identifying outliers as well.

At operation 576, the location of the identified patient anatomy points are calculated using an alternate method. Examples of alternate methods include inverse ellipse calculations and forward ellipse calculations. These example techniques no longer use the assumption that the estimated patient anatomy points is disposed at a location that projects to the midpoint between the emitting and receiving transducers on the transducer array plane. Instead, these techniques are based on determining an ellipsoid surface representing all of the estimated patient anatomy points that would result in the measured time of flight between the emitting and receiving transducers. Using the inverse ellipse calculation, the surface of the ellipsoid is correlated to the determined patient anatomy points to identify the likely location on the ellipsoid surface of the estimated patient anatomy points. Other embodiments are possible as well.

At operation 578, a three-dimensional image of the patient anatomy is generated based on the determined anatomy locations. The three-dimensional image may be generated using any technique for converting a point cloud to a three-dimension model or other form of three-dimensional image.

Users of the system may view and analyze (e.g., identify and measure various anatomical features) the three-dimensional image of the patient anatomy. As an example, the three-dimensional image may be used during a procedure to prepare a tooth site to receive a dental restoration and the three-dimensional image may be used to determine whether the tooth site has been adequately prepared (e.g., proper margin type, adequate reduction, sufficient occlusal and interproximal space for a restoration formed with a desired material). In some embodiments, the system may analyze the three-dimensional image to determine whether the tooth site is adequately prepared based on predetermined requirements. The predetermined requirements may be based on information published by a manufacturer or may be based on using learning techniques to analyze previous restorations (e.g., by correlating various parameters to outcomes of the restoration after installation). In addition, in some embodiments, the image is compared to previously captured images. Additionally, in some embodiments, the image is aligned to and (optionally) subtracted from a previously captured image or vice versa. The results of the alignment and subtraction operations can accentuate the differences between two images (e.g., to view changes, such as movement, growth, damage, or deterioration in the patient anatomy during the time that elapsed between the images). For example, the comparison may be used to evaluate the effect of orthodontic therapy, implant therapy, temporomandibular joint therapy, etc. Further, the comparison can include external morphology, internal morphology, local chemistry, or data acquired using additional external sensors or other data sources. In some embodiments, data from multiple sources are displayed using a multi-layer or semi-transparent display. For example, the combination of soft tissue morphology and hard tissue morphology may be displayed using semi-transparent, multi-layered image reconstruction techniques. Additionally, in some embodiments, local chemistry may be displayed using color coding (e.g., of the semi-transparent, multi-layered image).

In some aspects, the patient's anatomy may include a marker that is coupled to an implant abutment. The marker can be used to determine the position of a recently placed implant. Additionally, the patient's anatomy may be imaged during implant placement surgery to guide the implant placement and evaluate the placement relative to a plan. In some embodiments, features of the patient's anatomy that are detected during a procedure (e.g., implant location, drill hole location and depth, etc.) are compared to a plan automatically by the system.

Additionally, a series of three-dimensional images of the patient anatomy may be captured and used to represent the movement of the patient anatomy (or a portion thereof). For example, the motion of the jaw can be represented by capturing a series of images when the patient's jaw is in different bite positions (e.g., centric, eccentric, excursive, etc.). Further, in some embodiments, the motion of the patient's anatomy is determined relative to another portion of the patient's anatomy. For example, the motion of the mandibular arch of the jaw may be determined relative to the maxillary arch. To facilitate determining the relative motion, the images may include a portion of the moving anatomy as well as a portion of the stationary anatomy. This series of images may be used to evaluate and treat the occlusion of the patient. Similarly, a series of three-dimensional images may be generated of the position of the temporomandibular joint when the patient's jaw is in various bite positions. Beneficially, these images and the information that can be extracted from them may be helpful in the diagnosis of existing conditions and treatment of malocclusion by dental prosthetics and orthodontics.

Figure 21:
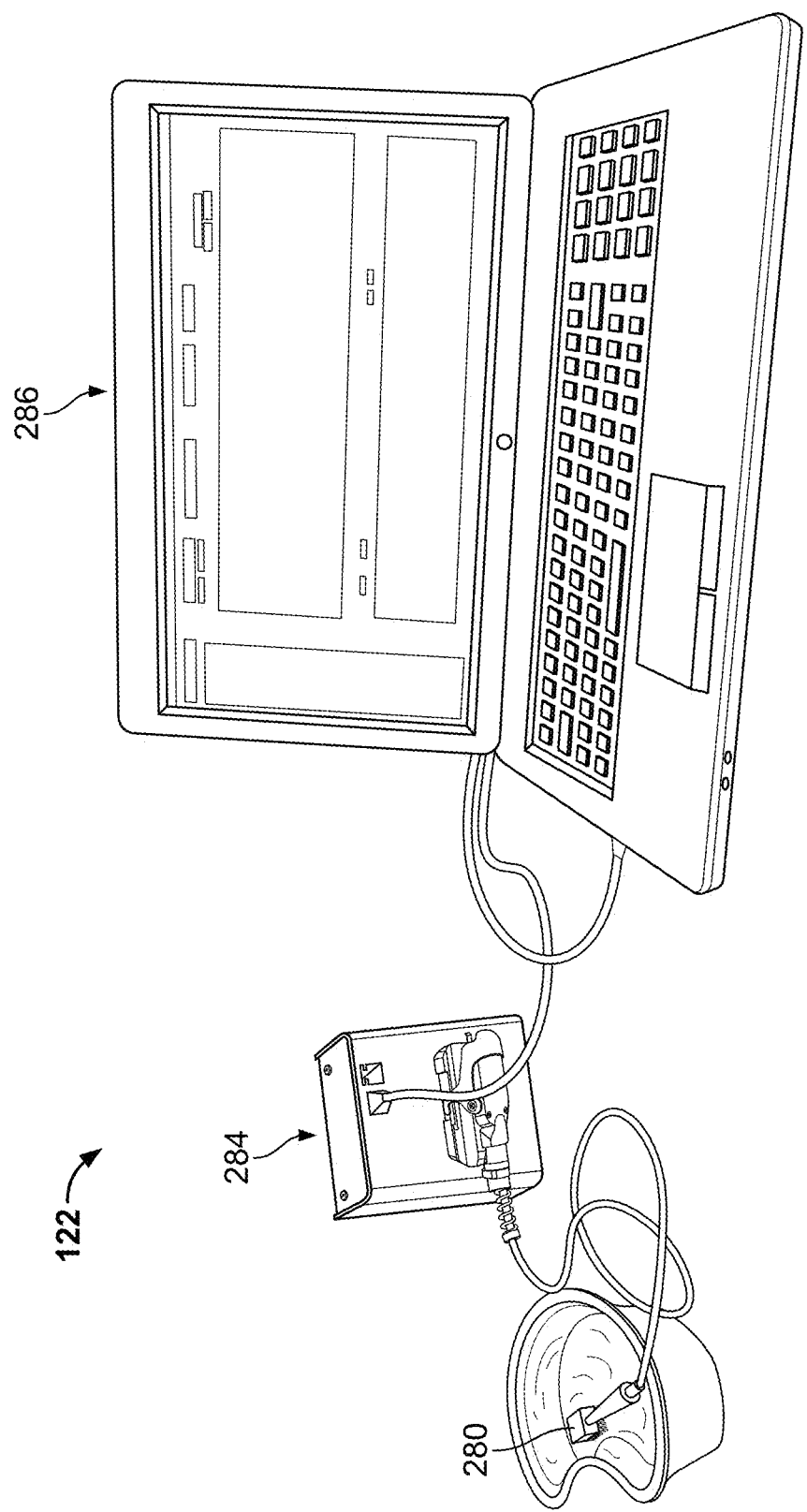
FIG. 21 illustrates an embodiment of the ultrasonic scanner of FIG. 1.

FIG. 21 illustrates an embodiment of the ultrasonic scanner 122, including the probe 280, the probe interface device 284, and the ultrasound capture system 286.

Figure 22:
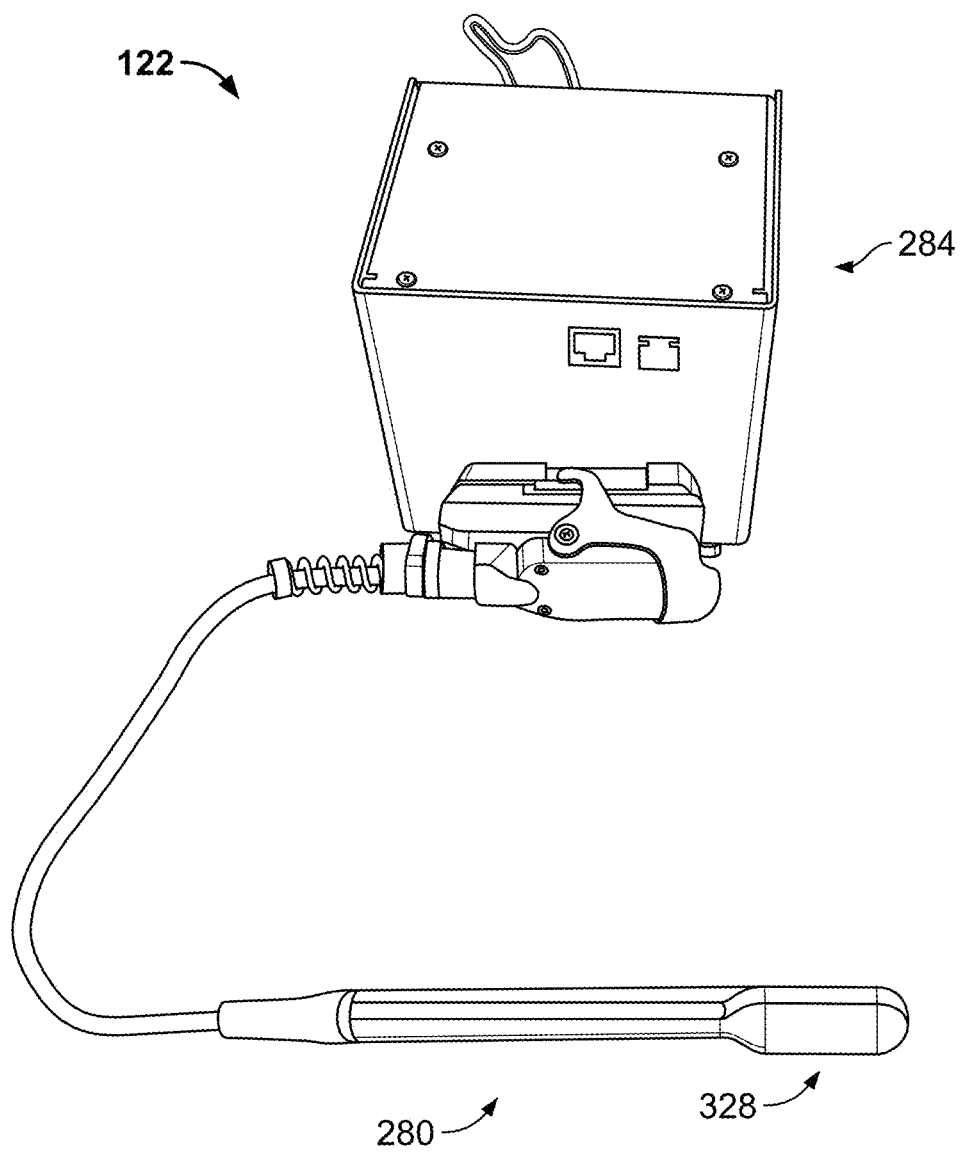
FIG. 22 illustrates another embodiment of the ultrasonic scanner of FIG. 1.

FIG. 22 illustrates another embodiment of the ultrasonic scanner 122, including the probe 280 and the probe interface device 284. Also shown is the transducer array 328.

Figure 23:
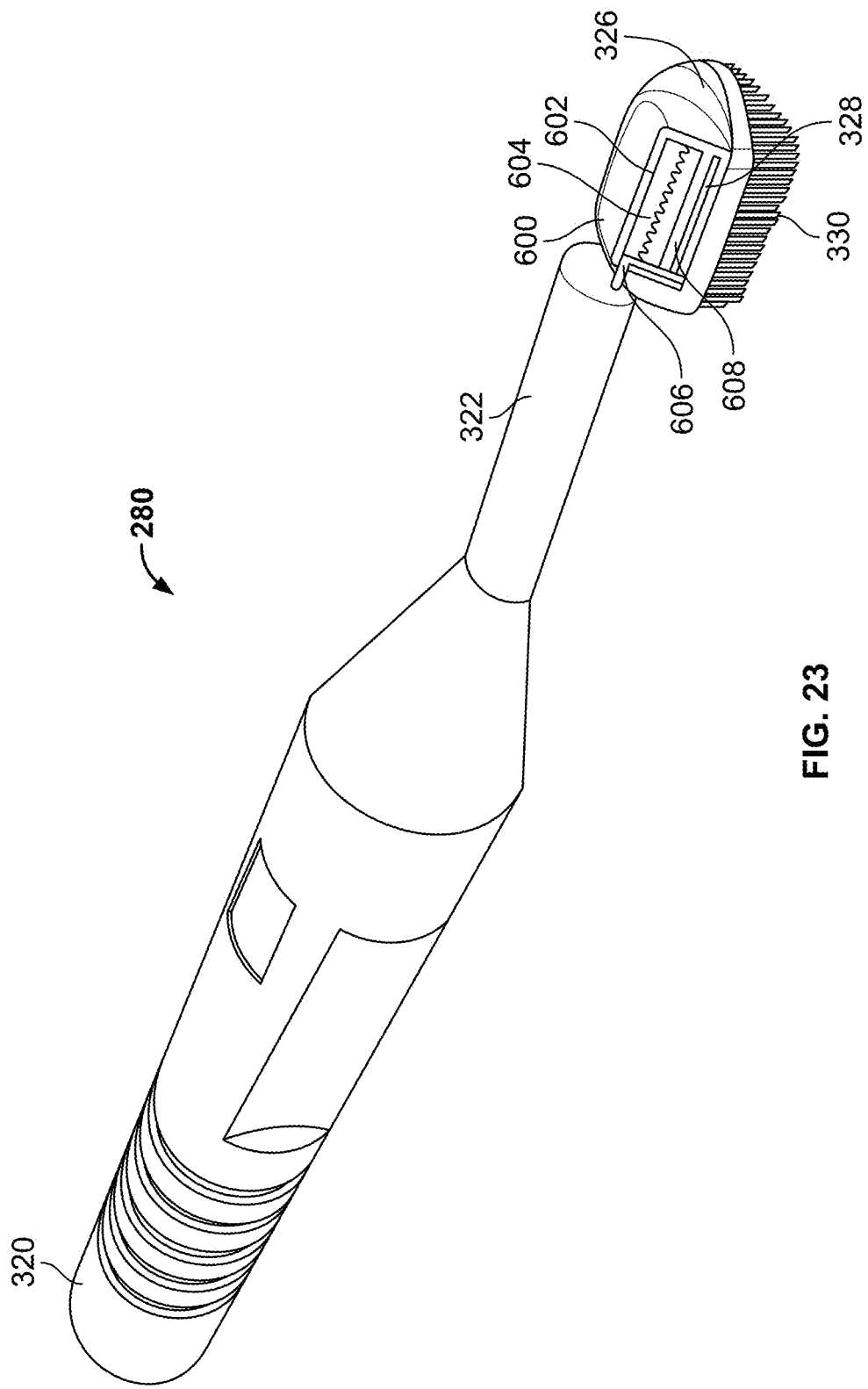
FIG. 23 illustrates an embodiment of the probe of FIG. 3 with a cutaway view of the tip.

FIG. 23 illustrates an embodiment of the probe 280 with a cutaway view of the tip 326, including a case 600, dampener 602, serrated backing 604, cable assembly 606, and electrode assembly 608. The case 600 operates to enclose the various components of the tip 326. The dampener 602 operates to absorb sound emitted from the backside of the transducer array 328. The dampener 602 can be formed from one or more materials that absorb sound. In some embodiments, the dampener 602 is formed from sand-filled epoxy. The serrated backing 604 operates to scatter any stray ultrasound waves, such as ultrasound waves that pass through the dampener 602. The cable assembly 606 operates to transmit excitation signals to the transducers of the transducer array 328 and to transmit signals received from the transducers of the transducer array 328. In some embodiments, the cable assembly 606 connects to the electrode assembly 608 which transports electrical energy to and from the transducers of the transducer array 328.

Figure 24:
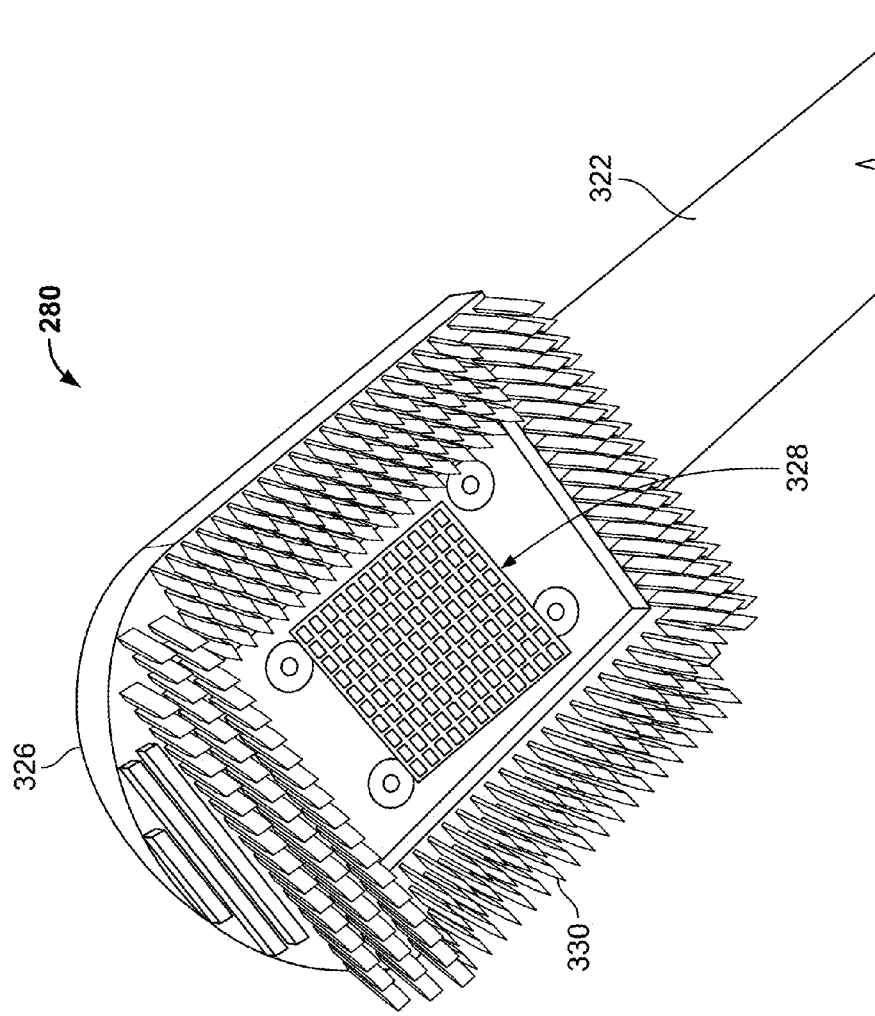
FIG. 24 is another illustration of an embodiment of the probe of FIG. 3.

FIG. 24 is another illustration of an embodiment of the probe of FIG. 3, including the transducer array 328 and the sheath 330 of the tip 326.

Although many of the examples provided herein related to imaging of the oral cavity, the technology and processes described herein are not so limited. For example, some embodiments of the probe 280 are configured to image the condyle of the patient. Some of these embodiments do not include a sheath to manage the field of view; rather an ultrasound transmission medium, such as a gel, lotion, or gel pad, is placed on the patient's skin and the probe is pressed into the gel. Examples of ultrasound transmission media include such as AQUASONIC® Ultrasound Transmission Gel, POLYSONIC® Ultrasound Lotion, and AQUAFLEX® Ultrasound Gel Pad all from Parker Laboratories, Inc. of Fairfield, N.J. Other ultrasound transmission media may be used as well. In yet other embodiments, the patient's appendage may be placed in a reservoir of liquid for imaging using the probe 280. For example, to image a patient's finger (or any other submersible body part), the finger may be placed in a reservoir of water, in which the probe 280 will also be placed during the imaging process.

Additionally, embodiments are used to image dental models and impressions. In some embodiments, the probe 280 is configured specifically to image dental impressions (e.g., by having a smaller probe tip that can fit in the impression). In some embodiments, the probe is configured for use in the medical office to evaluate various aspects of an impression such as whether the impression includes any voids or tears.

In an aspect, a system for ultrasound imaging of patient anatomy comprising: an ultrasound probe, comprising: a handle; an elongate member coupled to the handle; and a two-dimensional array of ultrasound transducers coupled to the elongate member, wherein the ultrasound transducers emit ultrasound when activated; and a full-matrix capture probe interface device communicatively coupled to the ultrasound probe, wherein the probe interface device is configured to activate at least one of the ultrasound transducers and to receive data corresponding to ultrasonic waves captured by a plurality of the ultrasound transducers.

In some embodiments, the system further comprises a sheath coupled to the elongate member and surrounding the two-dimensional array of ultrasound transducers and defining a space proximate to the two-dimensional array. In some embodiments, the sheath is formed from a flexible sheet. In some embodiments, the flexible sheet includes a first region and a second region, wherein the first region is coupled to the elongate member and has first durometer, and the second region is configured to contact the patient anatomy and has a second durometer, wherein the second durometer is harder than the first durometer. In some embodiments, the sheath is formed from a plurality bristles. In some embodiments, the system further comprises a fluid dispensing tube configured to dispense fluid into the space proximate to the two-dimensional array.

In some embodiments, the probe interface device is configured to sequentially activate each ultrasound transducer of the transducer array. In some embodiments, after activating one of the ultrasound transducers, the probe interface device is configured to receive data corresponding to ultrasonic waves captured by each of the of the ultrasound transducers. In some embodiments, the system further comprises an ultrasound capture system communicatively coupled to the probe interface device, wherein the ultrasound capture system receives data corresponding to the ultrasonic waves captured by each of the ultrasound transducers from the probe interface device and generates an image of a surface based on the received data. In some embodiments, the ultrasound capture system is further configured to correlate received data to patient biographical data or patient historical data.

In some embodiments, the image is a three-dimensional image and the ultrasound capture system generates the image based on a relationship between elapsed time, ultrasonic velocity, and distance. In some embodiments, the image is a three-dimensional image and the ultrasound capture system generates the image based on time of flight measurements and amplitude measurements. In some embodiments, amplitude data from the captured ultrasonic waves is combined with the three-dimensional image to determine characteristics of the anatomy. In some embodiments, the determined characteristics include tissue type. In some embodiments, the amplitude data is used to identify one or more of healthy enamel, cavities, gum tissues, tooth root structures, bones, and other supporting anatomical structures.

In some embodiments, the three-dimensional image comprises multiple layers that correspond to different tissue types. In some embodiments, the multiple layers are displayed using one or more of different colors or different transparency levels. In some embodiments, the multiple layers include a surface layer and at least one subsurface layer. In some embodiments, the system further includes an optical scanner and the three-dimensional image is generated by combining data captured by the probe interface device and the optical scanner. In some embodiments, the probe interface device is a parallax scanning system, a laser scanning system, or another type of optical scanning system. In some embodiments, the system is configured to image one or more of craniofacial anatomy of the patient, an oral cavity of the patient, a condyle of the patient, a restoration of the patient, an implant of the patient, and an extremity of the patient.

In some embodiments, the system further comprises: a vacuum system configured to collect fluids; and a fluid analysis system configured to analyze fluids collected by the vacuum system to generate fluid analysis data, wherein the fluid analysis data is associated with the data received by the full-matrix capture probe. In some embodiments, the fluid analysis data is correlated to one or more of clinical conditions or procedural information. In some embodiments, a three-dimensional image of the patient anatomy is generated and displayed using colors to indicate fluid analysis data. In some embodiments, the system is portable.

In another aspect, a method of imaging anatomy using an ultrasound probe that includes a plurality of ultrasound transducers arranged in a two-dimensional array, the method comprising: receiving an input signal indicating the probe is adjacent to the target anatomy; iterating through the plurality of transducers to capture ultrasound reflection data individually, wherein capturing ultrasound reflection data comprises emitting an ultrasound pulse with a single transducer of the plurality of transducers and capturing ultrasound reflection data using multiple transducers of the plurality of transducers; generating image segments from the captured ultrasound reflection data; and merging multiple image segments to form an image.

In some embodiments, the method further comprises: receiving an input signal indicating that image capture is complete; storing the image; and associating the image with patient data. In some embodiments, the method further comprises: comparing the generated image to a previously generated image for the patient; and displaying a visual representation of the changes between the generated image and the previously generated image. In some embodiments, the method further comprises transmitting the image to a remote computing device for fabrication of a physical model from the image.

In yet another aspect, a system for ultrasound imaging of patient dentition comprising: an ultrasound probe, comprising: a handle; an elongate member coupled to the handle; a two-dimensional array of ultrasound transducers coupled to the elongate member, wherein the ultrasound transducers emit ultrasound when activated; and a sheath coupled to the elongate member and surrounding the two-dimensional array of ultrasound transducers and defining a space proximate to the two-dimensional array; a full-matrix capture probe interface device communicatively coupled to the ultrasound probe, wherein the probe interface device is configured to sequentially activate each of the ultrasound transducers and to receive data corresponding to ultrasonic waves captured by each of the ultrasound transducers; and an ultrasound capture system communicatively coupled to the full-matrix capture probe interface device, wherein the ultrasound capture system receives data corresponding to the ultrasonic waves captured by each of the ultrasound transducers from the full-matrix capture probe interface device and generates an image of a surface based on the received data. In some embodiments, the ultrasound capture system generates an image of a surface and subsurface anatomy.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A system for ultrasound imaging of dental anatomy of a patient, the system comprising:
    an ultrasound probe, comprising:
        a handle;
        an elongate member coupled to the handle; and
        a tip at an end of the elongate member opposite the handle, the tip being configured to be inserted into an oral cavity of the patient, the tip comprising:
            a two-dimensional array of ultrasound transducers coupled to the tip, wherein the ultrasound transducers emit ultrasound when activated;
    a full-matrix capture probe interface device, including a circuit, communicatively coupled to the ultrasound probe, wherein the probe interface device is configured to activate at least one of the ultrasound transducers and to receive data corresponding to ultrasonic waves captured by a plurality of the ultrasound transducers; and
    an ultrasound capture system, including a circuit, communicatively coupled to the full-matrix capture probe interface device, wherein the ultrasound capture system receives data corresponding to the ultrasonic waves captured by each of the ultrasound transducers from the full-matrix capture probe interface device and generates an image of a surface from the received data based on identifying at least one patient anatomy point using an ellipsoid surface determined from the received data corresponding to the captured ultrasonic waves.

2. The system of claim 1, further comprising a sheath coupled to the tip and surrounding the two-dimensional array of ultrasound transducers and defining a space proximate to the two-dimensional array.

3. The system of claim 2, wherein the sheath is formed from a flexible sheet that includes a first region and a second region, wherein the first region is coupled to the tip and has a first durometer, and the second region is configured to contact the dental anatomy and has a second durometer, wherein the second durometer is harder than the first durometer.

4. The system of claim 2, wherein the sheath is formed from a plurality of bristles.

5. The system of claim 2, wherein the tip further comprises a fluid dispensing tube configured to dispense fluid into the space proximate to the two-dimensional array.

6. The system of claim 1, wherein the full-matrix capture probe interface device is configured to sequentially activate each ultrasound transducer of the transducer array.

7. The system of claim 6, wherein after activating one of the ultrasound transducers, the full-matrix capture probe interface device is configured to receive data corresponding to ultrasonic waves captured by each of the ultrasound transducers.

8. The system of claim 1, wherein the ultrasound capture system generates an image of a surface and a subsurface of the dental anatomy.

9. A system for ultrasound imaging of patient dentition comprising:
    an ultrasound probe, comprising:
        a handle;

an elongate member coupled to the handle;
a tip at an end of the elongate member opposite the handle, the tip being configured to be inserted into an oral cavity of the patient and maneuvered within the oral cavity during imaging, the tip comprising:
a two-dimensional array of ultrasound transducers coupled to the tip, wherein the ultrasound transducers emit ultrasound when activated; and
a sheath coupled to the tip and surrounding the two-dimensional array of ultrasound transducers and defining a space proximate to the two-dimensional array;
a full-matrix capture probe interface device, including a circuit, communicatively coupled to the ultrasound probe, wherein the probe interface device is configured to sequentially activate each of the ultrasound transducers and to receive data corresponding to ultrasonic waves captured by each of the ultrasound transducers; and
an ultrasound capture system, including a circuit, communicatively coupled to the full-matrix capture probe interface device, wherein the ultrasound capture system receives data corresponding to the ultrasonic waves captured by each of the ultrasound transducers from the full-matrix capture probe interface device and generates an image of a surface from the received data based on identifying at least one patient anatomy point using an ellipsoid surface determined from the received data corresponding to the captured ultrasonic waves.

10. The system of claim 9, wherein the ultrasound capture system generates an image of a surface and a subsurface of the patient dentition.

11. A method for ultrasound imaging of dental anatomy of a patient, the method comprising:
using a full-matrix capture probe interface device to activate at least one ultrasound transducer in a two-dimensional array of ultrasound transducers of an ultrasound probe that is communicatively coupled to the full-matrix capture probe interface device, the ultrasound probe including:
a handle;
an elongate member coupled to the handle; and
a tip disposed at an end of the elongate member opposite the handle, the two-dimensional array of ultrasound transducers being coupled to the tip and the ultrasound transducers being configured to emit ultrasound when activated;
receiving, by the full-matrix capture probe interface device, data corresponding to ultrasonic waves captured by a plurality of the ultrasound transducers; and
generating an image of a surface of the dental anatomy, by an ultrasound capture system that is communicatively coupled to the full-matrix capture probe interface device, the image being generated from the received data based on identifying at least one patient anatomy point using an ellipsoid surface determined from the received data corresponding to the captured ultrasonic waves.

12. The method of claim 11, wherein activating at least one of the ultrasound transducers comprises sequentially activating each ultrasound transducer of the two-dimensional array of ultrasound transducers.

13. The method of claim 12, wherein receiving data corresponding to the ultrasonic waves comprises receiving data captured by each of the ultrasound transducers after activating one of the ultrasound transducers.

14. The method of claim 11, further comprising generating an image of a subsurface of the dental anatomy from the received data.

* * * * *